(12) United States Patent
Zheng et al.

(10) Patent No.: US 11,512,078 B2
(45) Date of Patent: Nov. 29, 2022

(54) ADDITION SALT OF S1P1 RECEPTOR AGONIST AND CRYSTAL FORM THEREOF, AND PHARMACEUTICAL COMPOSITION

(71) Applicant: SUZHOU CONNECT BIOPHARMACEUTICALS, LTD., Jiangsu (CN)

(72) Inventors: Wei Zheng, San Diego, CA (US); Wubin Pan, Richmond (CA); Jiawang Guo, Taicang (CN)

(73) Assignee: SUZHOU CONNECT BIOPHARMACEUTICALS, LTD., Jiangsu (CN)

( * ) Notice: Subject to any disclaimer, the term of this patent is extended or adjusted under 35 U.S.C. 154(b) by 0 days.

(21) Appl. No.: 17/052,160

(22) PCT Filed: May 4, 2018

(86) PCT No.: PCT/CN2018/085617
§ 371 (c)(1),
(2) Date: Oct. 30, 2020

(87) PCT Pub. No.: WO2019/210511
PCT Pub. Date: Nov. 7, 2019

(65) Prior Publication Data
US 2021/0230152 A1 Jul. 29, 2021

(51) Int. Cl.
*C07D 413/10* (2006.01)

(52) U.S. Cl.
CPC ........ *C07D 413/10* (2013.01); *C07B 2200/13* (2013.01)

(58) Field of Classification Search
CPC .................................................. C07D 413/10
USPC ....................................................... 548/131
See application file for complete search history.

(56) References Cited

U.S. PATENT DOCUMENTS 10,280,158 B2    5/2019    Zheng et al.

FOREIGN PATENT DOCUMENTS

| CN | 103450171 A | 12/2013 |
|---|---|---|
| CN | 105315266 A | 2/2016 |
| CN | 108299412 A | 7/2018 |
| CN | 105348276 B | 5/2020 |
| WO | WO-2003105771 A2 | 12/2003 |
| WO | WO-2004035538 A1 | 4/2004 |

OTHER PUBLICATIONS

International Search Report completed Jan. 10, 2019, issued in PCT/CN2018/085617 (3 pages).
International Search Report and Written Opinion dated Dec. 17, 2014 for Application No. PCT/CN2014/086538, English Translation (14 pages).

*Primary Examiner* — Charanjit Aulakh
(74) *Attorney, Agent, or Firm* — Goodwin Procter LLP

(57) ABSTRACT

Disclosed in the present application are a salt form and a crystal form of an S1P1 receptor mediated disease or symptom drug 1-{2-fluoro-4-[5-(4-isobutylphenyl)-1,2,4-oxadiazole-3-yl]benzyl}-3-azetidinecarboxylic acid (formula A). Also disclosed in the present invention are a preparation method for the salt form or the crystal form, a pharmaceutical composition of the salt form or the crystal form, and use of the salt form or the crystal form in the preparation of a drug for treating and/or preventing an S1P1 receptor mediated disease or symptom.

(A)

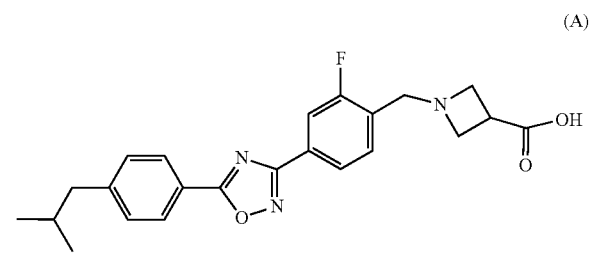

14 Claims, 6 Drawing Sheets

$2\theta\ (°)$ $2\theta\ (°)$ $2\theta\ (°)$ $2\theta\ (°)$

ADDITION SALT OF S1P1 RECEPTOR AGONIST AND CRYSTAL FORM THEREOF, AND PHARMACEUTICAL COMPOSITION

CROSS-REFERENCE TO RELATED APPLICATION(S)

The present application is a National Phase Patent Application of International Patent Application Number PCT/CN2018/085617, filed on May 4, 2018, the entire contents of which are incorporated herein by reference.

TECHNICAL FIELD

The present application belongs to the technical field of chemical preparation and crystallization of a medicament. In particular, it relates to a salt form of a medicament for an S1P1 receptor mediated disease or condition and a crystal form thereof, and further relates to a method for preparing the salt form or the crystal form, and a pharmaceutical composition and use of the salt form or the crystal form.

BACKGROUND OF THE INVENTION

The chemical formula of 1-{2-fluoro-4-[5-(4-isobutylphenyl)-1,2,4-oxadiazole-3-yl]benzyl}-3-azetidinecarboxylic acid is $C_{23}H_{24}FN_3O_3$, having a molecular weight of 409.45, and a chemical structure represented by the following formula A.

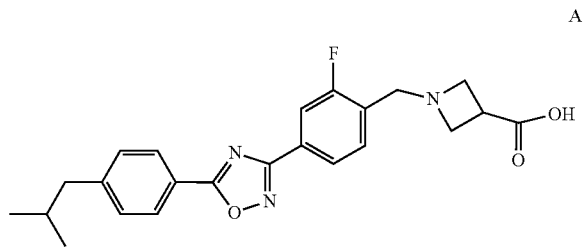 [SMILES: CC(C)Cc1ccc(-c2nc(-c3ccc(CN4CC(C(=O)O)C4)c(F)c3)no2)cc1]

A

Herein, the term "1-{2-fluoro-4-[5-(4-isobutylphenyl)-1,2,4-oxadiazole-3-yl]benzyl}-3-azetidinecarboxylic acid" and the term "compound represented by formula A" are interchangeable.

The compound represented by formula A has agonist activity on and selection specificity for S1P1 receptor, and has a significantly shortened in-vivo half-life, so it is an excellent second-generation S1P1 receptor agonist. A large number of studies have shown that there are many kinds of S1P1 receptor agonists, which can bind to homologous receptors expressed on lymphocytes, lead to S1P1 receptor internalization, and in turn prevent lymphocytes from being exported. Therefore, S1P1 receptor agonists can reduce the ability of human body to initiate immune response by blocking the transport of lymphocytes, so they can be used as immunosuppressants in the treatment of various autoimmune diseases.

Theoretically, a salt can be formed by the compound represented by formula A and one or more acid compounds represented by formula $X_mH_n$, in which H is a dissociative hydrogen ion, X is a pharmaceutically-acceptable anion, and m and n are natural numbers. A salt can also be formed by the compound represented by formula A and one or more pharmaceutically-acceptable cations, such as alkali metal ions or other pharmaceutically-acceptable organic cations.

Identification, preparation, a composition and use of the compound represented by formula A are disclosed in patent document CN103450171A (which is incorporated herein by reference in its entirety). Specifically, a method for preparing the compound is disclosed in Example 2. 12 crystal forms of the compound represented by formula A are disclosed in patent document CN105315266A (which is incorporated herein by reference in its entirety). However, studies by the present inventors found that, those free alkalis had very low water solubility, having a solubility of 1.1 μg/mL in water at 25° C., and presented different stable forms in different solvent environments. For example, the most stable crystal form in water was crystal form I, while the most stable crystal form in an organic solvent was crystal form IV. Therefore, the limitations of the compound include that free alkalis of the compound are insoluble in water and have an evident crystal polymorphism. Therefore, it is of great practical significance to study salt forms of the compound represented by formula A, to improve certain undesirable physicochemical or biopharmaceutical properties of the medicament, such as the solubility or dissolution of the medicament and the polymorph phenomenon, and the like, by the salt of the compound represented by formula A formed.

SUMMARY OF THE INVENTION

In view of the defects of the prior art, the first object of the present application is to provide a salt form of a compound represented by formula A and a crystal form thereof. The salt form of the compound represented by formula A and the crystal form thereof have one or more improved properties, especially in terms of polymorphism, solubility, crystal form stability and chemical stability, and the like. For example, compared with other conventional salt forms, such as potassium salt, calcium salt, hydrochloride, citrate and phosphate, the salt form of the compound represented by formula A according to the present application has one or more improved properties in hygroscopicity, solubility and thermal stability (melting point and decomposition temperature).

The second object of the present application is to provide a method for preparing the salt form of the compound represented by formula A. Since the compound represented by formula A has a low solubility in most solvents and temperature has no obvious effect on improving the solubility, it is difficult to form a salt using a conventional solution-solution mixing reaction. The method for preparing the salt form according to the present application adopts a variety of ways including suspension-solution, solid-solution, solid-solid-solvent, suspension-suspension and solid-suspension mixing reactions to form a salt, uses a crystal form detection method to monitor salt formation completeness, and adopts ion chromatography to confirm the ratio between the compound represented by formula A and counter ion. Compared with conventional salt forming methods, the method for preparing the salt form of the compound represented by formula A has good controllability in salt formation of the low-solubility compound.

The third object of the present application is to provide a pharmaceutical composition of the salt form of the compound represented by formula A and the crystal form, and use thereof.

According to the objects of the present application, the present application provides a sodium salt of 1-{2-fluoro-4-[5-(4-isobutylphenyl)-1,2,4-oxadiazole-3-yl]benzyl}-3-azetidinecarboxylic acid, which is a compound formed by the compound represented by formula A and sodium ion in a molar ratio of 1:1, having a structure represented by the following formula:

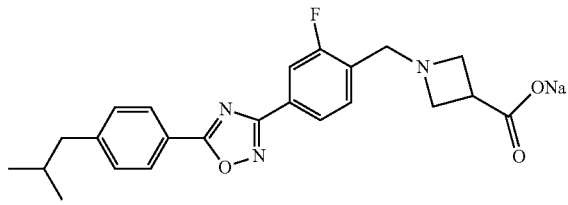

Herein, the term "sodium salt of 1-{2-fluoro-4-[5-(4-isobutylphenyl)-1,2,4-oxadiazole-3-yl]benzyl}-3-azetidinecarboxylic acid" and the term "sodium salt of the compound represented by formula A" are interchangeable.

The sodium salt of the compound represented by formula A according to the present application substantially is in a crystal state, and preferably is an anhydrate, a hydrate, or a non-solvate. More preferably, according to the objects of the present application, the present application provides a crystal form of the sodium salt of the compound represented by formula A. The crystal form has an X-ray powder diffraction pattern characterized by angle 2θ having characteristic peaks at the following positions: 4.4±0.2°, 6.6±0.2°, 14.7±0.2, and 17.2±0.2°.

Further preferably, the present application provides a crystal form of the sodium salt of the compound represented by formula A. The crystal form has an X-ray powder diffraction pattern characterized by angle 2θ having characteristic peaks at the following positions with relative intensities as follows:

| 2θ | Relative intensity % |
|---|---|
| 4.4 ± 0.2° | 100 |
| 6.6 ± 0.2° | 80.8 |
| 14.7 ± 0.2° | 11.5 |
| 15.4 ± 0.2° | 2.6 |
| 17.2 ± 0.2° | 8.6 |

Without limitation, a typical example of the crystal form of the sodium salt of the compound represented by formula A has an X-Ray Powder Diffraction (XRPD) pattern as illustrated in FIG. 2. More preferably, the crystal form of the sodium salt of the compound represented by formula A has a Fourier transform infrared spectrum having characteristic peaks at wavenumbers 1560 $cm^{-1}$, 1505 $cm^{-1}$, 1476 $cm^{-1}$, 1417 $cm^{-1}$, 1365 $cm^{-1}$, 1276 $cm^{-1}$, 885 $cm^{-1}$, 849 $cm^{-1}$, and 756 $cm^{-1}$.

According to the objects of the present application, the present application provides a method for preparing the sodium salt of the compound represented by formula A or the crystal form thereof. The method includes the following steps: mixing the compound represented by formula A and sodium hydroxide in a molar ratio of 1:1-1:5 in a solvent selected from the group consisting of an alcohol, a ketone, an ether, water, a nitrile, or a mixture thereof for reaction, removing the solvent after the reaction is complete, and performing drying.

According to particular embodiments of the present application, for the preparation of the salt form, in the operation of removing the solvent after reaction is complete, part of the solvent can be removed firstly, then centrifugation is performed after cooling, and the obtained solid is dried; or, all of the solvent is removed after reaction is complete, a solvent is added to the solid obtained again to prepare a slurry, then centrifugation is performed, and the obtained solid is dried.

According to particular embodiments of the present application, for the preparation of the crystal form, in the operation of removing the solvent after reaction is complete, part of the solvent can be removed firstly, then cooling (for example, to room temperature) is performed to precipitate a solid, and the obtained solid is dried.

Preferably, the solvent is selected from the group consisting of methanol, ethanol, acetone, diethyl ether, water, acetonitrile, or a mixture thereof.

Preferably, the molar ratio of the compound represented by formula A to sodium hydroxide is 1:1.0-1:1.3.

Preferably, the reaction is performed at 10-60° C., more preferably at room temperature.

Preferably, the reaction is performed under stirring, and the stirring time is 1-48 h, more preferably 3-24 h.

Preferably, the drying is performed under vacuum, and the drying temperature is 10-60° C., more preferably 10-40° C.

Preferably, the drying time is 1-48 h, more preferably 1-24 h.

Preferably, the ratio of mass of the compound represented by formula A to volume of the solvent in the method is 1 mg:1 mL-50 mg:1 mL, more preferably 2.5 mg:1 mL-41 mg:1 mL.

The "removing the solvent" can be performed by using conventional technical means in the art, for example, filtration, volatilization, centrifugation, nitrogen blowing or spin drying. Preferably, the solvent is removed through nitrogen blowing, volatilization or filtration. Preferably, the "removing the solvent" is performed at an experiment temperature of 10-60° C.

The sodium salt of the compound represented by formula A and the crystal form thereof have the following beneficial effects.

1) The crystal polymorphism of the sodium salt of the compound represented by formula A according to the present application is not evident.

2) The sodium salt of the compound represented by formula A according to the present application has a solubility of 10 mg/mL in water at 25° C. Compared with the known free state of the compound represented by formula A, the sodium salt has obviously improved solubility in water and better bioavailability.

3) The sodium salt of the compound represented by formula A according to the present application has a solubility of 10 mg/mL in water at 25° C. Compared with conventional salt forms such as calcium salt of the compound represented by formula A, hydrochloride of the compound represented by formula A, citrate of the compound represented by formula A, and phosphate of the compound represented by formula A etc., the sodium salt has significantly improved solubility in water and better bioavailability.

4) Compared with the free state of the compound represented by formula A, the crystal form of the sodium salt of the compound represented by formula A according to the present application is stable in aqueous systems, so it has a better practical value in wet granulation or suspension formulation.

5) The crystal form of the sodium salt of the compound represented by formula A according to the present application remains unchanged in appearance, XRPD pattern and melting point after being stored for 4 months under conditions of room temperature and relative humidity of 10%-

90%. It is indicated that the sodium salt of the compound represented by formula A and the crystal form thereof according to the present application have good storage stability, and can be better at avoiding quality, safety and stability problems of the active ingredient itself and preparations containing the sodium salt of the compound represented by formula A or the crystal form thereof during drug manufacture and/or storage, etc., for example, impurity crystal forms and difference in solubility etc.

The present application further provides a pharmaceutical composition, comprising the sodium salt of the compound represented by formula A and/or the crystal form thereof, and optionally at least one pharmaceutically acceptable carrier or excipient.

The present application further provides use of the sodium salt of the compound represented by formula A and/or the crystal form thereof in the manufacture of a medicament for treating and/or preventing an S1P1 receptor mediated disease or condition.

The present application further provides a method for treating and/or preventing an S1P1 receptor mediated disease or condition, including administering to a subject in need thereof the sodium salt of the compound represented by formula A and/or the crystal form thereof provided by the present application. Preferably, the subject is a mammal; more preferably, the subject is a human.

According to the objects of the present application, the present application provides a sulfate of 1-{2-fluoro-4-[5-(4-isobutylphenyl)-1,2,4-oxadiazole-3-yl]benzyl}-3-azetidinecarboxylic acid, which is a compound formed by the compound represented by formula A and sulfuric acid in a molar ratio of 2:1, having a structure represented by the following formula:

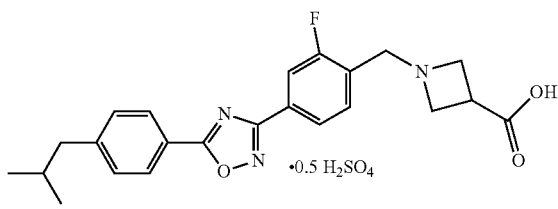 [SMILES: CC(C)Cc1ccc(-c2nc(-c3ccc(CN4CC(C(=O)O)C4)c(F)c3)no2)cc1]

Herein, the term "sulfate of 1-{2-fluoro-4-[5-(4-isobutylphenyl)-1,2,4-oxadiazole-3-yl]benzyl}-3-azetidinecarboxylic acid" and the term "sulfate of the compound represented by formula A" are interchangeable.

The sulfate of the compound represented by formula A according to the present application substantially is in a crystal state, and preferably is an anhydrate, a hydrate, or a non-solvate. More preferably, according to the objects of the present application, the present application provides a crystal form of the sulfate of the compound represented by formula A. With Cu-Kα radiation, the crystal form has an X-ray powder diffraction pattern characterized by angle 2θ having characteristic peaks at the following positions: 5.4±0.2°, 8.1±0.2°, 14.8±0.2°, 16.7±0.2°, and 18.3±0.2°.

More preferably, the crystal form of the sulfate of the compound represented by formula A has an X-ray powder diffraction pattern characterized by angle 2θ having characteristic peaks at the following positions: 5.4±0.2°, 8.1±0.2°, 14.8±0.2°, 15.6±0.2°, 16.7±0.2°, 18.3±0.2°, 21.0±0.2°, 22.0±0.2°, 22.9±0.2°, 25.2±0.2°, and 26.3±0.2°.

Further preferably, the present application provides a crystal form of the sulfate of the compound represented by formula A. The crystal form has an X-ray powder diffraction pattern characterized by angle 2θ having characteristic peaks at the following positions with relative intensities as follows:

| 2θ | Relative intensity % |
|---|---|
| 5.4 ± 0.2° | 62.3 |
| 8.1 ± 0.2° | 47.3 |
| 10.9 ± 0.2° | 9.9 |
| 14.8 ± 0.2° | 100 |
| 15.6 ± 0.2° | 12.5 |
| 16.7 ± 0.2° | 58.6 |
| 18.3 ± 0.2° | 18.2 |
| 19.7 ± 0.2° | 15.5 |
| 20.5 ± 0.2° | 10.1 |
| 21.0 ± 0.2° | 17.4 |
| 22.0 ± 0.2° | 18.1 |
| 22.9 ± 0.2° | 39.3 |
| 25.2 ± 0.2° | 37.4 |
| 26.3 ± 0.2° | 36.5 |

Without limitation, a typical example of the crystal form of the sulfate of the compound represented by formula A has an X-Ray Powder Diffraction (XRPD) pattern as illustrated in FIG. 6.

The crystal form of the sulfate of the compound represented by formula A has a Fourier transform infrared spectrum having characteristic peaks at wavenumbers 1733 $cm^{-1}$, 1438 $cm^{-1}$, 1346 $cm^{-1}$, 1230 $cm^{-1}$, 1184 $cm^{-1}$, 1109 $cm^{-1}$, 1063 $cm^{-1}$, 1009 $cm^{-1}$, 885 $cm^{-1}$, 854 $cm^{-1}$, and 758 $cm^{-1}$.

According to the objects of the present application, the present application provides a method for preparing the sulfate of the compound represented by formula A or the crystal form thereof. The method includes the following steps: forming a suspension or solution of the compound represented by formula A and a suspension or solution of sulfuric acid in a solvent selected from the group consisting of an alcohol, a ketone, a cyclic ether, a nitrile, water, or a mixture thereof respectively, mixing the suspension or solution in a molar ratio of 1:0.4-1:10 of the compound represented by formula A to sulfuric acid for reaction, removing the solvent after the reaction is complete, and performing drying.

According to particular embodiments of the present application, for the preparation of the salt form, in the operation of removing the solvent after reaction is complete, part of the solvent can be removed firstly, then cooling or centrifugation is performed, and the obtained solid is dried; or, all of the solvent is removed after reaction is complete, a solvent is optionally added to the solid obtained again to prepare a slurry, then centrifugation is performed, and the obtained solid is dried.

According to particular embodiments of the present application, for the preparation of the crystal form, in the operation of removing the solvent after reaction is complete, all of the solvent can be removed firstly, then water is added for ultrasonication, centrifugation is performed, and the obtained solid is dried.

Preferably, the solvent is selected from the group consisting of methanol, ethanol, n-propanol, acetone, tetrahydrofuran, water, acetonitrile, or a mixture thereof.

Preferably, the molar ratio of the compound represented by formula A to sulfuric acid is 1:0.4-1:7.9.

Preferably, the reaction is performed at −10-60° C., more preferably at 10-40° C. Preferably, the reaction is performed under stirring, and the stirring time is 1-72 h, more preferably 1-24 h.

Preferably, the drying temperature is 10-60° C., more preferably 10-40° C.

Preferably, the drying time is 1-48 h, more preferably 1-24 h.

Preferably, the ratio of mass of the compound represented by formula A to volume of the solvent in the method is 1 mg:1 mL-50 mg:1 mL, more preferably 4 mg:1 mL-35 mg:1 mL.

The "removing the solvent" can be performed by using conventional technical means in the art, for example, filtration, volatilization, centrifugation, nitrogen blowing or spin drying. Preferably, the solvent is removed through nitrogen blowing, volatilization or filtration. Preferably, the removing the solvent is performed at an experiment temperature of 10-60° C.

The "sulfuric acid" refers to concentrated sulfuric acid, which has a concentration of 98% (wt. %) and is commercially available.

The sulfate of the compound represented by formula A and the crystal form thereof have the following beneficial effects:

1) The crystal polymorphism of the sulfate of the compound represented by formula A according to the present application is not evident.

2) The sulfate of the compound represented by formula A according to the present application has a solubility of 19 μg/mL in water at 25° C. Compared with the known free state of the compound represented by formula A, the sulfate has obviously improved solubility in water and better bioavailability.

3) The sulfate of the compound represented by formula A according to the present application has a solubility of 19 μg/mL in water at 25° C. Compared with conventional salt forms such as calcium salt of the compound represented by formula A, hydrochloride of the compound represented by formula A, citrate of the compound represented by formula A, and phosphate of the compound represented by formula A, etc. the sulfate has significantly improved solubility in water and better bioavailability.

4) The sulfate of the compound represented by formula A according to the present application has a weight gain of 0.7% at relative humidity of 20%-80%. Compared with conventional salt forms such as potassium salt of the compound represented by formula A, calcium salt of the compound represented by formula A, hydrochloride of the compound represented by formula A, citrate of the compound represented by formula A, and phosphate of the compound represented by formula A etc., the sulfate has a lower hygroscopic weight gain and thus better storage stability.

5) The crystal form of the sulfate of the compound represented by formula A according to the present application is stable in aqueous systems, so it has a better practical value in wet granulation or suspension formulation.

6) The crystal form of the sulfate of the compound represented by formula A according to the present application remains unchanged in appearance, XRPD pattern and melting point after being stored for 1 month under conventional, high-temperature (60° C.) and accelerated conditions (40° C.-75% relative humidity). It is indicated that the sulfate of the compound represented by formula A and the crystal form thereof according to the present application have good storage stability, and can be better at avoiding quality, safety and stability problems of the active ingredient itself and preparations containing the sulfate of the compound represented by formula A or the crystal form thereof during drug manufacture and/or storage, etc., for example, impurity crystal forms and difference in solubility etc.

The present application further provides a pharmaceutical composition comprising the sulfate of the compound represented by formula A and/or the crystal form thereof, and optionally at least one pharmaceutically acceptable carrier or excipient.

The present application further provides use of the sulfate of the compound represented by formula A and/or the crystal form thereof in the manufacture of a medicament for treating and/or preventing an S1P1 receptor mediated disease or condition.

The present application further provides a method for treating and/or preventing an S1P1 receptor mediated disease or condition, including administering to a subject in need thereof the sulfate of the compound represented by formula A and/or the crystal form thereof provided by the present application. Preferably, the subject is a mammal; more preferably, the subject is a human.

According to the objects of the present application, the present application provides a maleate of 1-{2-fluoro-4-[5-(4-isobutylphenyl)-1,2,4-oxadiazole-3-yl]benzyl}-3-azetidinecarboxylic acid, which is a compound formed by the compound represented by formula A and maleic acid in a molar ratio of 1:1, having a structure represented by the following formula:

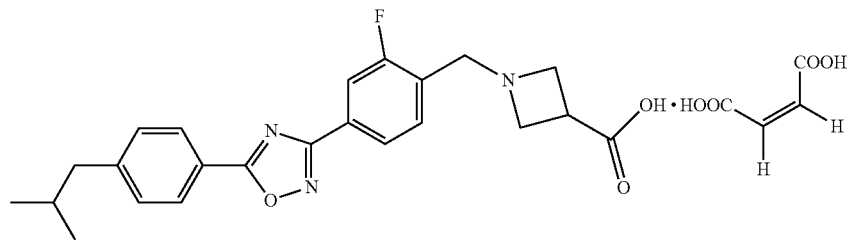 [SMILES: CC(C)Cc1ccc(-c2nc(-c3ccc(CN4CC(C(=O)O)C4)c(F)c3)no2)cc1 ; O=C(O)/C=C\C(=O)O]

Herein, the term "maleate of 1-{2-fluoro-4-[5-(4-isobutylphenyl)-1,2,4-oxadiazole-3-yl]benzyl}-3-azetidinecarboxylic acid" and the term "maleate of the compound represented by formula A" are interchangeable.

The maleate of the compound represented by formula A according to the present application substantially is in a crystal state, and preferably is an anhydrate, a hydrate, or a non-solvate. More preferably, according to the objects of the present application, the present application provides a crystal form of the maleate of the compound represented by formula A. With Cu-Kα radiation, the crystal form has an X-ray powder diffraction pattern characterized by angle 2θ having characteristic peaks at the following positions: 10.6±0.2°, 16.3±0.2°, 19.5±0.2°, 21.5±0.2°, and 26.9±0.2°.

More preferably, the crystal form of the maleate of the compound represented by formula A has an X-ray powder diffraction pattern characterized by angle 2θ having characteristic peaks at the following positions: 7.0±0.2°, 10.6±0.2°, 13.6±0.2°, 16.3±0.2°, 19.5±0.2°, 20.1±0.2°, 21.5±0.2°, 24.5±0.2°, and 26.9±0.2°.

Further preferably, the present application provides a crystal form of the maleate of the compound represented by formula A. The crystal form has an X-ray powder diffraction pattern characterized by angle 2θ having characteristic peaks at the following positions with relative intensities as follows:

| 2θ | Relative intensity % |
| --- | --- |
| 5.3 ± 0.2° | 3.4 |
| 7.0 ± 0.2° | 5.8 |
| 10.6 ± 0.2° | 100 |
| 13.6 ± 0.2° | 6.6 |
| 14.5 ± 0.2° | 3.2 |
| 16.3 ± 0.2° | 12.2 |
| 19.5 ± 0.2° | 37.7 |
| 20.1 ± 0.2° | 8.6 |
| 20.7 ± 0.2° | 2.8 |
| 21.5 ± 0.2° | 18.3 |
| 24.5 ± 0.2° | 11.4 |
| 24.7 ± 0.2° | 9.6 |
| 25.3 ± 0.2° | 1.8 |
| 26.1 ± 0.2° | 1.9 |
| 26.9 ± 0.2° | 34.5 |
| 28.7 ± 0.2° | 2.2 |

Without limitation, a typical example of the crystal form of the maleate of the compound represented by formula A has an X-Ray Powder Diffraction (XRPD) pattern as illustrated in FIG. 10.

The crystal form of the maleate of the compound represented by formula A has a Fourier transform infrared spectrum having characteristic peaks at wavenumbers 1734 $cm^{-1}$, 1574 $cm^{-1}$, 1485 $cm^{-1}$, 1439 $cm^{-1}$, 1364 $cm^{-1}$, 1346 $cm^{-1}$, 1080 $cm^{-1}$, 1003 $cm^{-1}$, 893 $cm^{-1}$, 871 $cm^{-1}$, 757 $cm^{-1}$, and 729 $cm^{-1}$.

According to the objects of the present application, the present application provides a method for preparing the maleate of the compound represented by formula A or the crystal form thereof. The method includes the following steps: forming a suspension or solution of the compound represented by formula A and a suspension or solution of maleic acid in a solvent selected from the group consisting of an alcohol, a ketones, an ether (including a cyclic ether), an ester, water, or a mixture thereof respectively, mixing the suspension or solution a molar ratio of 1:1-1:5 of the compound represented by formula A to maleic acid for reaction, removing the solvent after the reaction is complete, and performing drying.

Preferably, the solvent is selected from the group consisting of ethanol, acetone, diethyl ether, water, ethyl acetate, 1,4-dioxane, or a mixture thereof.

Preferably, the molar ratio of the compound represented by formula A to maleic acid is 1:1.0-1:2.6.

Preferably, the reaction is performed at −10-60° C., more preferably at 10-40° C. Preferably, the reaction is performed under stirring, and the stirring time is 10-72 h, more preferably 10-24 h.

Preferably, the drying temperature is 10-60° C., more preferably 10-40° C.

Preferably, the drying time is 1-48 h, more preferably 1-24 h.

Preferably, the ratio of mass of the compound represented by formula A to volume of the solvent in the method is 1 mg:1 mL-50 mg:1 mL, more preferably 4 mg:1 mL-26 mg:1 mL.

The maleate of the compound represented by formula A and the crystal form thereof have the following beneficial effects:

1) The crystal polymorphism of the maleate of the compound represented by formula A according to the present application is not evident.

2) The maleate of the compound represented by formula A according to the present application has a solubility of 16 μg/mL in water at 25° C. Compared with the known free state of the compound represented by formula A, the maleate has obviously improved solubility in water and better bioavailability.

3) The maleate of the compound represented by formula A according to the present application has a solubility of 16 μg/mL in water at 25° C. Compared with conventional salt forms such as calcium salt of the compound represented by formula A, hydrochloride of the compound represented by formula A, citrate of the compound represented by formula A, and phosphate of the compound represented by formula A etc., the maleate has significantly improved solubility in water and better bioavailability.

4) The maleate of the compound represented by formula A according to the present application has a weight gain of 0.4% at relative humidity of 20%-80%. Compared with conventional salt forms such as potassium salt of the compound represented by formula A, calcium salt of the compound represented by formula A, hydrochloride of the compound represented by formula A, citrate of the compound represented by formula A, and phosphate of the compound represented by formula A etc., the maleate has a lower hygroscopic weight gain and thus better storage stability.

5) The crystal form of the maleate of the compound represented by formula A according to the present application is stable in aqueous systems, so it has a better practical value in wet granulation or suspension formulation.

6) The crystal form of the maleate of the compound represented by formula A according to the present application remains unchanged in appearance, XRPD pattern and melting point after being stored for 1 month under conventional, high-temperature (60° C.) and accelerated conditions (40° C.-75% relative humidity). It is indicated that the maleate of the compound represented by formula A and the crystal form thereof according to the present application have good storage stability, and can be better at avoiding the quality, safety and stability problems of the active ingredient itself and preparations containing the maleate of the compound represented by formula A or the crystal form thereof during drug manufacture and/or storage, etc., for example, impurity crystal forms and difference in solubility etc.

The present application further provides a pharmaceutical composition comprising the maleate of the compound represented by formula A and/or the crystal form thereof, and optionally at least one pharmaceutically acceptable carrier or excipient.

The present application further provides use of the maleate of the compound represented by formula A and/or the crystal form thereof in the manufacture of a medicament for treating and/or preventing an S1P1 receptor mediated disease or condition.

The present application further provides a method for treating and/or preventing an S1P1 receptor mediated disease or condition, including administering to a subject in need thereof the maleate of the compound represented by formula A and/or the crystal form thereof provided by the present application. Preferably, the subject is a mammal; more preferably, the subject is a human.

In any method for preparing the sodium salt of the compound represented by formula A and the crystal form of the sodium salt of the compound represented by formula A, the sulfate of the compound represented by formula A and the crystal form of the sulfate of the compound represented by formula A, the maleate of the compound represented by formula A, and the crystal form of the maleate of the compound represented by formula A according to the present application.

Unless otherwise specified, "room temperature" refers to a temperature of about 10-30° C.

The "cyclic ether" can be tetrahydrofuran, 1,4-dioxane, etc.

The "stirring" can be performed by using a conventional method in the art. For example, the stirring includes magnetic stirring and mechanical stirring; and the stirring speed is 50-1800 rpm, preferably 300-900 rpm.

The "removing the solvent" can be performed by using a conventional method in the art, such as filtration, volatilization, centrifugation, nitrogen blowing or spin drying. The "filtration" generally refers to suction filtration conducted at room temperature at pressure less than atmospheric pressure, preferably at pressure less than 0.09 MPa. The "spin drying" generally refers to rotary evaporation at pressure less than atmospheric pressure, preferably at pressure less than 0.09 MPa. The "nitrogen blowing" generally refers to feeding nitrogen through a nitrogen blowing instrument and a liquid is volatilized to dry by the rapid flow of nitrogen fed. The specific operation of "centrifugation" is as follows: a sample to be separated is placed in a centrifuge tube and is centrifuged, for example, at the speed of 6000 rpm until the solid is completely settled at the bottom of the centrifuge tube. The specific operation of "volatilization" is as follows: a sample solution placed in an open container is volatilized at different temperatures until the solvent is dried. The "removing the solvent" is performed at an experiment temperature of preferably 10-60° C.

The "drying" can be performed by using conventional technical means in the art, such as room-temperature drying, air-blow drying or drying under reduced pressure. It can be performed at reduced pressure or atmospheric pressure, preferably at pressure less than 0.09 MPa. The drying instrument and method are not limited. The drying instrument can be a ventilator, an air-blow drying oven, a spray dryer, a fluidized bed dryer or a vacuum oven; and the drying can be performed at reduced pressure or non-reduced pressure, preferably at pressure less than 0.09 MPa.

The "crystal form" in the present application means that the compound has a unique and ordered molecular arrangement or configuration in lattice, as proved by the X-ray powder diffraction pattern characterization illustrated. As well known to those skilled in the art, there may be experimental errors depending on instrument conditions, sample preparation and sample purity. The angle 2θ of the peak in XRD pattern usually varies slightly with the instrument and sample. According to different instruments and different samples and the like, the difference of the peak angle may be 1°, 0.8°, 0.5°, 0.3°, 0.1°, etc, and usually an error of ±0.2° is allowed; therefore difference of the peak angles cannot be used as the only standard. The relative intensity of the peak may vary with the sample, sample preparation and other experimental conditions, so the order of the peak intensities cannot be used as the only or decisive factor. The influence due to sample height and other experimental factors may result in an overall shift of the peak angles, and a certain extent of shift is usually allowed. Therefore, those skilled in the art can understand that any crystal form with the same or similar characteristic peaks as those in the X-ray powder diffraction pattern provided in the present application belongs to the scope of the present application. "Single crystal form" refers to a single crystal form as detected by X-ray powder diffraction.

The new salt form of the compound represented by formula A according to the present application is substantially pure and single, and is substantially not mixed with any other crystal form or amorphous state. "Substantially pure" in the present application, when used to refer to a new crystal form, means that the new crystal form accounts for at least 80% (by weight) of the compound, further at least 90% (by weight), especially at least 95% (by weight), and particularly at least 99% (by weight).

The starting material in the present application, i.e., the compound represented by formula A, can be prepared according to the preparation method disclosed in patent document CN103450171A.

Further, the present application provides a pharmaceutical composition, comprising a therapeutically or prophylactically effective amount of one or more selected from the group consisting of the salt forms or the crystal forms and amorphous forms thereof according to the present application, or the salt forms and/or the crystal forms and amorphous forms thereof prepared by the method according to the present application, and optionally at least one pharmaceutically acceptable carrier or excipient. The salt forms of the compound represented by formula A and the crystal forms thereof include the sodium salt of the compound represented by formula A, the crystal form of the sodium salt of the compound represented by formula A, the sulfate of the compound represented by formula A, the crystal form of the sulfate of the compound represented by formula A, the maleate of the compound represented by formula A, and the crystal form of the maleate of the compound represented by formula A. Besides, the pharmaceutical composition can further comprise other pharmaceutically acceptable salts of the compound represented by formula A, crystal forms of the salts or amorphous forms of the salts.

The above pharmaceutical composition can be prepared into certain dosage forms, preferably into dosage forms by oral administration, parenteral administration (including subcutaneous, intramuscular and intravenous), rectal administration, transdermal administration, buccal administration and nasal administration, including but not limited to solid dosage form, liquid dosage form, semi-liquid dosage form, aerosol or suppository, etc. For example, the dosage forms suitable for oral administration include tablets, capsules, granules, powder, pills, powders, lozenges, syrups or suspensions; the dosage forms suitable for parenteral administration include aqueous or non-aqueous solutions or emulsions; the dosage forms suitable for rectal administration include suppositories using hydrophilic or hydrophobic carriers; the dosage forms suitable for transdermal administration include ointments and creams; the dosage forms suitable for nasal administration include aerosols and sprays. As needed, the above dosage forms can be adapted for rapid release, delayed release or regulated release of active ingredients.

The pharmaceutically acceptable carriers in the present application include solid carriers, specifically including but not limited to diluents, such as starch, pre-gelatinized starch, lactose, powdered cellulose, microcrystalline cellulose, calcium hydrogen phosphate, tricalcium phosphate, mannitol, sorbitol, and sugar, and the like; binders, such as Arabic gum, guar gum, gelatin, polyvinyl pyrrolidone, hydroxypropyl cellulose, hydroxypropyl methyl cellulose, and polyethylene glycol, and the like; disintegrants, such as starch, sodium hydroxyacetate starch, pre-gelatinized starch, crosslinked povidone, crosslinked carboxymethyl cellulose sodium, and colloidal silica, and the like; lubricants, such as stearic acid, magnesium stearate, zinc stearate, sodium benzoate, and sodium acetate, and the like; flow aids, such as colloidal silica, and the like; complex forming agents, such as various grades of cyclodextrins and resins; release rate control agents, such as hydroxypropyl cellulose, hydroxymethyl cellulose, hydroxypropyl methyl cellulose, ethyl cellulose, methyl cellulose, methyl methacrylate, and wax, and the like. The pharmaceutically acceptable carriers in the present application further include liquid carriers, specifically including but not limited to solvents of aqueous, oily or alcohol solution, such as sterile water, normal saline solution, glucose solution, mannitol solution, vegetable oil, cod liver oil, ethanol, propanol, and glycerin, and the like. In addition, other carriers such as polyethylene glycol and polypropylene glycol, and the like may be used. Other pharmaceutically acceptable carriers may also be selected according to different dosage forms, for example, including but not limited to film-forming agents, plasticizers, colorants, flavoring agents, viscosity regulators, preservatives, antioxidants, penetrants, buffers, etc. Each carrier must be acceptable, compatible with other ingredients in the formulation and harmless to patients.

The pharmaceutical composition can be prepared by using a method well-known to those skilled in the art. When the pharmaceutical composition is prepared, the sodium salt of the compound represented by formula A, the crystal form of the sodium salt of the compound represented by formula A, the sulfate of the compound represented by formula A, the crystal form of the sulfate of the compound represented by formula A, the maleate of the compound represented by formula A, the crystal form of the maleate of the compound represented by formula A or a combination thereof is mixed with one or more pharmaceutically acceptable carriers, and optionally is mixed with one or more other active pharmaceutical ingredients. Solid preparations can be prepared by processes such as mixing and granulation etc., while liquid or semi-liquid dosage forms can be prepared by processes such as mixing, dissolving, dispersing and emulsifying etc.

Further, the present application provides use of the salt form and/or the crystal form and amorphous form thereof according to the present application, or the salt form and/or the crystal form and amorphous form thereof obtained by using the preparation method according to the present application in the manufacture of a medicament for treating and/or preventing an S1P1 receptor mediated disease or condition. The salt form and the crystal form and amorphous form thereof include the sodium salt of the compound represented by formula A, the crystal form of the sodium salt of the compound represented by formula A, the sulfate of the compound represented by formula A, the crystal form of the sulfate of the compound represented by formula A, the maleate of the compound represented by formula A, the crystal form of the maleate of the compound represented by formula A, or a combination thereof. The S1P1 receptor mediated disease or condition is selected from the group consisting of rheumatoid arthritis, multiple sclerosis, inflammatory enteritis, autoimmune diseases, chronic inflammatory diseases, asthma, inflammatory neuropathy, arthritis, transplantation, segmental ileitis, ulcerative colitis, lupus erythematosus, psoriasis, ischemia-reperfusion injury, solid tumors, angiogenesis related diseases, vascular diseases, pain symptoms, acute viral diseases, inflammatory bowel diseases, insulin and non-insulin dependent diabetes mellitus and other related immune diseases. Preferably, the disease or condition is selected from the group consisting of multiple sclerosis, rheumatoid arthritis, inflammatory enteritis and psoriasis.

Further, the present application provides a method for treating and/or preventing an S1P1 receptor mediated disease or condition, including administering to a subject in need thereof a therapeutically or prophylactically effective amount of the salt and/or the crystal form thereof or a combination thereof or the pharmaceutical composition according to the present application. The salt and the crystal form and amorphous form thereof include the sodium salt of the compound represented by formula A, the crystal form of the sodium salt of the compound represented by formula A, the sulfate of the compound represented by formula A, the crystal form of the sulfate of the compound represented by formula A, the maleate of the compound represented by formula A, the crystal form of the maleate of the compound represented by formula A, or a combination thereof. The S1P1 receptor mediated disease or condition is selected from the group consisting of rheumatoid arthritis, multiple sclerosis, inflammatory enteritis, autoimmune diseases, chronic inflammatory diseases, asthma, inflammatory neuropathy, arthritis, transplantation, segmental ileitis, ulcerative colitis, lupus erythematosus, psoriasis, ischemia-reperfusion injury, solid tumors, angiogenesis related diseases, vascular diseases, pain symptoms, acute viral diseases, inflammatory bowel diseases, insulin and non-insulin dependent diabetes mellitus and other related immune diseases. Preferably, the disease or condition is selected from the group consisting of multiple sclerosis, rheumatoid arthritis, inflammatory enteritis and psoriasis. The subject includes but is not limited to mammals. The crystal form and amorphous form or the combination thereof or the pharmaceutical composition provided by the present application can be used together with other therapies or therapeutic agents. Moreover, the dosage of the compound or the pharmaceutical composition required for the treatment, prevention or alleviation etc. generally depends on the specific compound administered, the patient, specific disease or condition and severity thereof, administration route and frequency, and needs to be determined by the attending doctor according to specific situations.

DETAILED DESCRIPTION OF PREFERRED EMBODIMENTS

Figure 1:
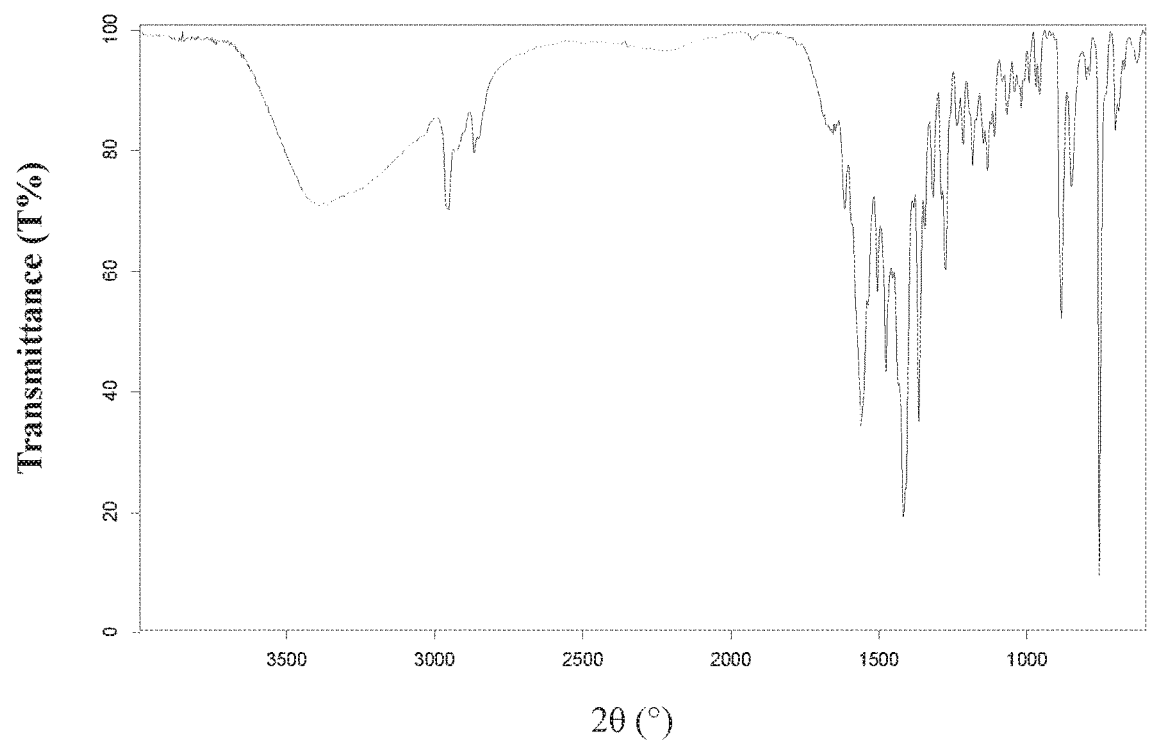
FIG. 1 is an IR pattern of the sodium salt of the compound represented by formula A according to Example 3 of the present application.

The following Examples will facilitate a further understanding of the present application, and are not used to limit the present application.

Detection instruments and methods:

X-Ray Powder Diffraction (XPRD): the instrument was Bruker D8 Advance diffractometer. Samples were tested at room temperature. Detection conditions were as follows: angle range: 3-40° 2θ; step size: 0.02°2θ; speed: 0.2 second/step.

Differential Scanning Calorimetry (DSC) data were collected with TA Instruments Q200 MDSC. The detection method used was as follows: 1-10 mg of a sample was placed in an airtight small-hole aluminum crucible, and the temperature of the sample was increased from room temperature to 250° C. at a heating rate of 10° C./min under the protection of 40 mL/min dry $N_2$.

Thermogravimetric Analysis (TGA) data were collected with TA Instruments Q500 TGA. The detection method used was as follows: 5-15 mg of a samples was placed in a platinum crucible, and a segmented high-resolution detection method was adopted in which the temperature of the sample was increased from room temperature to 300° C. at a heating rate of 10° C./min under the protection of 40 mL/min dry $N_2$.

1H Nuclear Magnetic Resonance ($^1$HNMR) data were obtained with Bruker Avance II DMX 400 MHZ nuclear magnetic resonance spectrometer. 1-5 mg of a sample was weighed and dissolved in about 0.5 mL of deuterated reagent in a sample tube for nuclear magnetic resonance, and was detected.

Infrared Spectroscopy (IR) data were collected with Bruker Tensor 27. Both instrument control software and data analysis software were OPUS. Infrared absorption spectrum in a range of 600-4000 $cm^{-1}$ was collected with ATR equipment generally.

Dynamic Vapor Sorption (DVS) data and isothermal sorption analysis data were collected with TA Instruments Q5000 TGA. The detection method used was as follows: 1-10 mg of a sample was placed in a platinum crucible, and weight change with the change of relative humidity from 20% to 80% was detected.

HPLC solubility data were collected with Agilent 1260 high performance liquid chromatograph. The chromatographic column used was Poroshell 120 EC-C18 (2.7*50 mm, 4.6 μm), the detection wavelength was 254 nm, column temperature for detection was 40° C., flow rate was 1.5 mL/min, and the sample volume was 5 μL. A sample was dissolved in mobile phase B to prepare a sample solution of a concentration about 0.45 mg/mL, and HPLC detection was performed according to the following gradient elution mode to obtain concentration in the sample.

|  | Time (min) | % mobile phase A | % mobile phase B |
| --- | --- | --- | --- |
| Gradient | 0 | 95 | 5 |
|  | 0.2 | 95 | 5 |
|  | 3.7 | 5 | 95 |
|  | 6 | 5 | 95 |
|  | 6.01 | 95 | 5 |
|  | 9.0 | 95 | 5 |
| Mobile phase A | Water:trifluoroacetic acid = 1000:0.5 | | |
| Mobile phase B | Acetonitrile:trifluoroacetic acid = 1000:0.5 | | |

Ion Chromatography (IC) data were collected with Dionex ICS-900. Both workstation and analysis software were Chromeleon Console. Ion content detection was performed by using External Standard Method.

Ultrasonication operations described in the Examples can facilitate the dissolution of the samples. The equipment was an ultrasonic cleaner, and the ultrasonication was performed for 15 min at power of 40 kHz.

Preparation Example 1: Preparation of the Compound Represented by Formula A

The compound represented by formula A can be prepared according to the preparation method described in Example 2 of patent document CN103450171A.

Specifically, at room temperature, a solution of 2-fluoro-4-[5-(4-isobutylphenyl)-1,2,4-oxadiazole-3-yl]-benzaldehyde (9.0 g, 27.8 mmol), azetidine-3-carboxylic acid (2.8 g, 27.8 mmol) and acetic acid (10 mL) in methanol-tetrahydrofuran (200 mL/200 mL) was stirred for 2 h. Then a solution (600 mL) of sodium cyanoborohydrate (10.3 g, 163.5 mmol) in methanol (600 mL) was added to the reaction mixture and then resulting mixture was stirred for additional 16 h at room temperature. Filtration was performed to obtain a filter cake, and the filter cake was washed with methanol (100 mL), and dried to obtain 2.0 g of white solid product.

$^1$H-NMR (400 MHz, CD3OD) δ: 8.13 (d, J=8.4 Hz, 2H), 8.05 (m, 1H), 7.97 (m, 1H), 7.68 (t, J=8.0 Hz, 7.6 Hz, 1H), 7.42 (d, J=8.4 Hz, 2H), 4.40 (s, 2H), 4.15 (m, 4H), 3.41 (m, 1H), 2.61 (d, J=7.2 Hz, 2H), 1.95 (m, 1H), 0.94 (d, J=7.2 Hz, 6H) indicated the product was the compound represented by formula A, i.e., 1-{2-fluoro-4-[5-(4-isobutylphenyl)-1,2,4-oxadiazole-3-yl]benzyl}-3-azetidinecarboxylic acid.

Preparation Example 2: Screening and Preparation of Salt Forms of the Compound Represented by Formula A 2.1 Salt Screening According to the structure of the compound represented by formula A, 12 type I acids and 3 type I alkalis were selected for a salt screening experiment. Experiment setup and results were shown in Table 1.

TABLE 1

| | Salt screening experiment setup and results | | | | |
|---|---|---|---|---|---|
| Counter ion | Solvent/molar ratio of reactants (free state of the compound represented by formula A: counter ion) | Temperature | Post-treatment | Result | IC characterization of salt |
| Citric acid | Ethanol/1:2.4, isopropanol/1:2.2, water/1:2.5, acetone/1:1.3, or acetonitrile/1:1.3 | Room temperature | Nitrogen blowing or filtration | Salt could be formed in acetone, and no salt was formed in other solvents or salt could not be obtained repeatedly. | 1:1 |
| Phosphoric acid | Ethanol/1:4.0 or 1:1.3, acetone/1:4.3 or 1:1.3, acetonitrile/1:1.2, water/1:8.5, diethyl ether:ethanol = 5:1/1:3.0, tetrahydrofuran/1:6.4, isopropanol/1:1.0 | Room temperature or 40° C. | Nitrogen blowing or filtration | Salt could be formed in acetone or ethanol, and no salt was formed in other solvents or salt could not be obtained repeatedly. | 1:1 |
| Sulfuric acid | Methanol/1:4.1, ethanol/1:3.0, n-propanol/1:7.9, water/1:3.2 or 1:3.0, acetone:water = 5:1/1:3.3, tetrahydrofuran:water = 5:1/1:3.1, acetonitrile:water = 4:1/1:3.2 | Room temperature or 40° C. | Nitrogen blowing or filtration | Salt could be formed in all solvents. | 2:1 |
| Hydrochloric acid | Methanol/1:10.0, methanol/1:9.8, isopropanol/1:5.9, water/1:5.7 or 1:3.9, acetone/1:4.8 or 1:3.2, diethyl ether/1:4.5, ethyl acetate/1:5.9, acetonitrile/1:3.2 | Room temperature | Nitrogen blowing or filtration | Salt could be formed in methanol, isopropanol, acetone or ethanol, and no salt was formed in other solvents or salt could not be obtained repeatedly. | 1:1 |
| Maleic acid | Acetone/1:1.2, ethanol/1:1.3, water/1:2.1, diethyl ether/1:1.2, ethyl acetate/1:2.0, 1,4-dioxane/1:2.6 | Room temperature | Nitrogen blowing or filtration | Salt could be formed in all solvents. | 1:1 |
| Sodium | Methanol/1:1.3 or 1:1.0, water/1:1.3, acetone:water = 4:1/1:1.2, diethyl ether:ethanol = 4:1/1:1.3, ethyl acetate:ethanol = 4:1/1:3.2, acetonitrile:water = 4:1/1:1.4 | Room temperature | Nitrogen blowing or filtration or subjecting filtrate obtained after filtration to nitrogen blowing | Salt could be formed in all solvents except ethyl acetate:ethanol. | 1:1 |
| Potassium | Methanol/1:1.0, water/1:1.4, acetone:water = 4:1/1:1.4, isopropyl acetate:ethanol = 4:1/1:1.0, 1,4-dioxane:water = 4:1/1:1.2, acetonitrile:water = 4:1/1:1.3 | Room temperature | Nitrogen blowing or filtration or subjecting filtrate obtained after filtration to nitrogen blowing | Salt could be formed in all solvents. | 1:1 |
| Calcium | Methanol/1:0.6 or 1:1.6, water/1:1.2 or 1:2.8 or 1:1.4 or 1:1.3, ethanol/1:1.7 or 1:1.3, isopropanol/1:1.5 | Room temperature | Nitrogen blowing or filtration | Salt could be formed in methanol, water and ethanol. | 2:1 |

TABLE 1-continued

Salt screening experiment setup and results

| Counter ion | Solvent/molar ratio of reactants (free state of the compound represented by formula A: counter ion) | Temperature | Post-treatment | Result | IC characterization of salt |
|---|---|---|---|---|---|
| D-gluconic acid | Methanol/1:1.2, ethanol:water = 1:1/1:2.8, water/1:2.2, acetone:water = 5:1/1:1.1, tetrahydrofuran:water = 5:1/1:2.3, acetonitrile:water = 4:1/1:2.0 | Room temperature or 40° C. | Nitrogen blowing | No salt was formed. | |
| L-malic acid | Ethanol/1:2.5, acetone/1:1.2, diethyl ether/1:1.2, 1,4-dioxane/1:3.0, acetonitrile/1:2.1 | Room temperature or 40° C. | Nitrogen blowing | No salt was formed. | |
| Succinic acid | Methanol/1:1.3, water/1:2.7, acetone/1:1.3, diethyl ether/1:2.0, tetrahydrofuran/1:3.1, tetrahydrofuran/1:1.5 | Room temperature or 40° C. | Nitrogen blowing or filtration | No salt was formed. | |
| L-tartaric acid | Ethanol/1:1.3, water/1:1.2, acetone/1:1.5, diethyl ether/1:2.5, tetrahydrofuran/1:1.5, acetonitrile/1:2.1 | Room temperature or 40° C. | Nitrogen blowing or filtration | No salt was formed. | |
| Glacial acetic acid | Ethanol/1:2.7, water/1:8.1, acetone/1:7.3, diethyl ether/1:9.6, tetrahydrofuran/1:7.5, tetrahydrofuran/1:6.0 | Room temperature or 40° C. | Nitrogen blowing | No salt was formed. | |
| Fumaric acid | Ethanol/1:2.8, water/1:1.4, acetone/1:2.5, diethyl ether/1:1.2, ethyl acetate/1:2.0 | Room temperature or 40° C. | Nitrogen blowing | No salt was formed. | |
| Hippuric acid | Isopropanol/1:1.2, water/1:2.1, acetone/1:2.1, diethyl ether/1:2.1, tetrahydrofuran/1:2.2, acetonitrile/1:2.0 | Room temperature or 40° C. | Nitrogen blowing | No salt was formed. | |

2.2 Preparation of Some Salts

Acetone and water were selected as reaction solvents, free state of the compound represented by formula A and counter ions in a molar ratio of 1:1.2 were used for salt formation, and the ratio in the salt formed was detected by using IC. A citrate of the compound represented by formula A, a phosphate of the compound represented by formula A, a hydrochloride of the compound represented by formula A, a potassium salt of the compound represented by formula A and a calcium salt of the compound represented by formula A were prepared.

Example 1: Preparation of Sodium Salt of the Compound Represented by Formula A 14.50 mg of the compound represented by formula A prepared in Preparation Example 1 were weighed and added into 0.5 mL of methanol, and the obtained mixture was stirred to form a suspension. A sodium hydroxide solution (1.75 mg of sodium hydroxide was added into 0.45 mL of methanol) was dropped into the suspension of the compound represented by formula A in methanol, and the obtained mixture was stirred for about 10 min at room temperature to form a clear solution, which was stirred for additional 3 h. Then the solvent was removed from the solution by nitrogen blowing at room temperature, to obtain 0.2 mL of a colorless transparent clear solution, which was cooled to 5° C. to obtain a suspension. Centrifugation was performed, and the obtained solid was dried for 16 h at room temperature under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 2: Preparation of Sodium Salt of the Compound Represented by Formula A 40.71 mg of the compound represented by formula A prepared in Preparation Example 1 were weighed and added into 0.4 mL of methanol, and the obtained mixture was stirred to form a suspension. A sodium hydroxide solution (4.0 mg of sodium hydroxide was added into 2.8 mL of methanol) was dropped into the suspension of the compound represented by formula A in methanol, and the obtained mixture was stirred for about 1 h at room temperature to form a clear solution. The solution was stirred for additional 2 h, then filtration was performed, and the solvent was removed from the filtrate through volatilization at room temperature to obtain 0.2 mL of a suspension. Centrifugation was performed, and the obtained solid was dried for 24 h at room temperature under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 3: Preparation of Sodium Salt of the Compound Represented by Formula A 4.9 mg of sodium hydroxide was weighed and added into 1.0 mL of water, and ultrasonication was performed to obtain a clear solution. The clear solution was dropped into 40.7 mg of the compound represented by formula A prepared in Preparation Example 1, and the obtained mixture was stirred for 24 h at room temperature. Filtration was performed, and the solvent was removed from the filtrate by nitrogen blowing at 60° C. to obtain 0.2 mL of a light yellow transparent clear solution. The solution was cooled to room temperature to precipitate a solid, then centrifugation was performed, and the solid obtained was dried for 1 h at 40° C. under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

An IR pattern of the sodium salt was as illustrated in FIG. 1.

Figure 2:
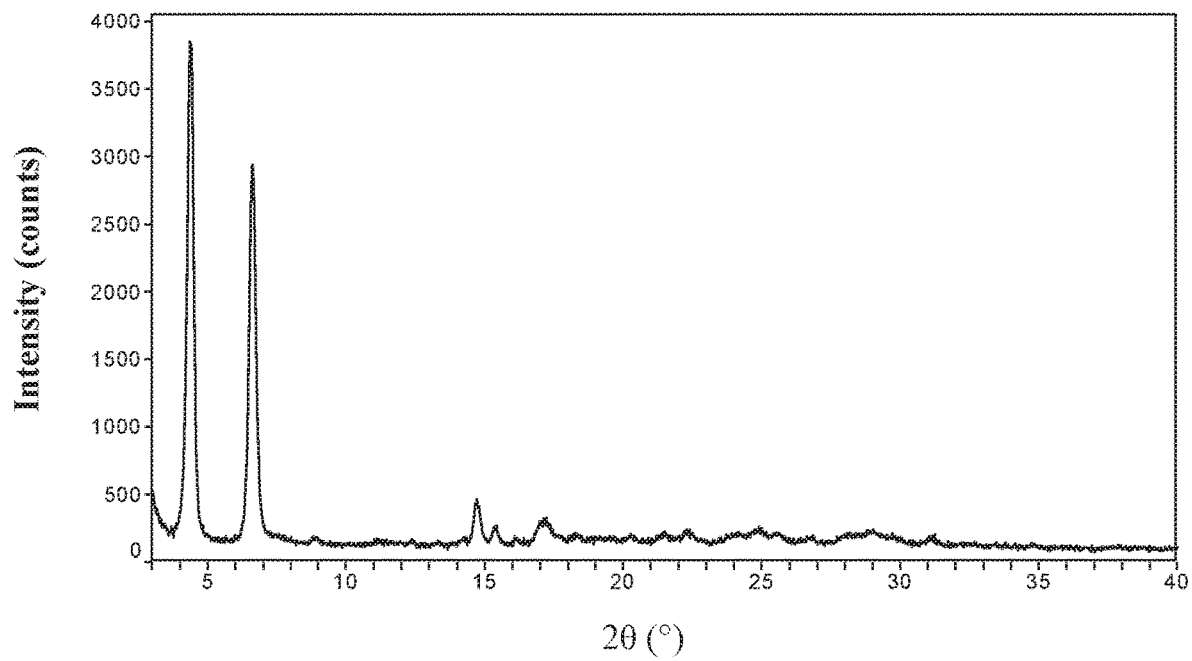
FIG. 2 is an XRPD pattern of the sodium salt of the compound represented by formula A according to Example 3 of the present application.

An XRD pattern of the sodium salt was as illustrated in FIG. 2.

Figure 3:
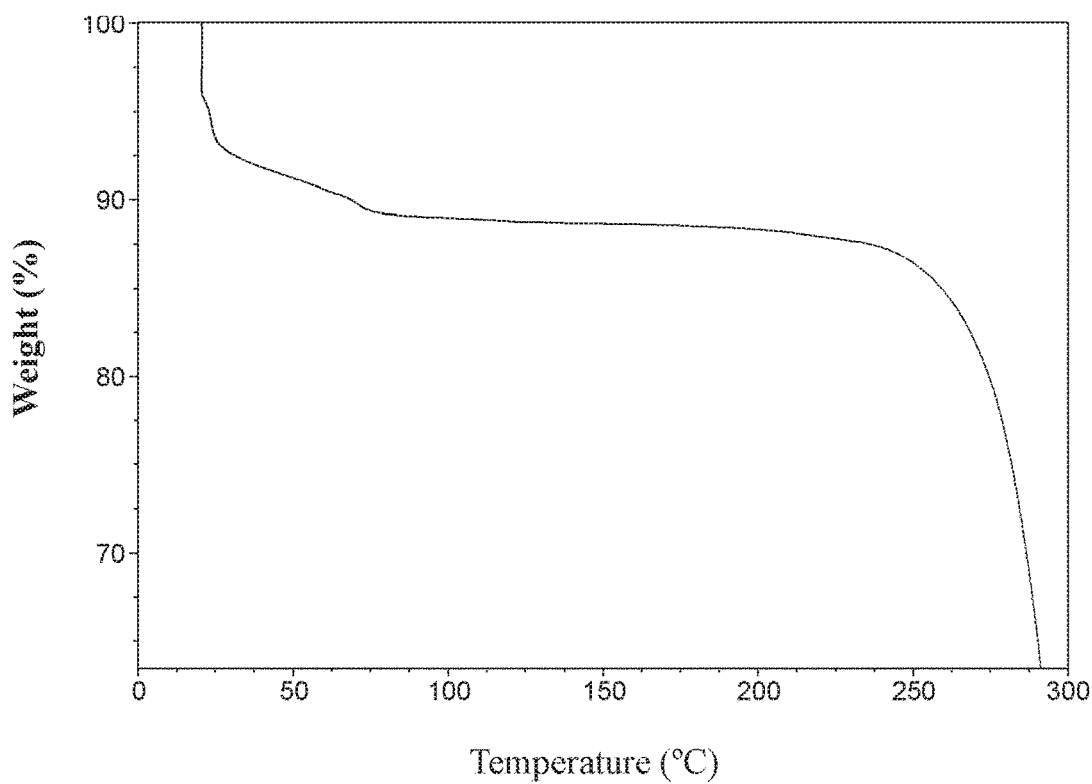
FIG. 3 is a TGA pattern of the sodium salt of the compound represented by formula A according to Example 3 of the present application.

A TGA pattern of the sodium salt was as illustrated in FIG. 3.

Figure 4:
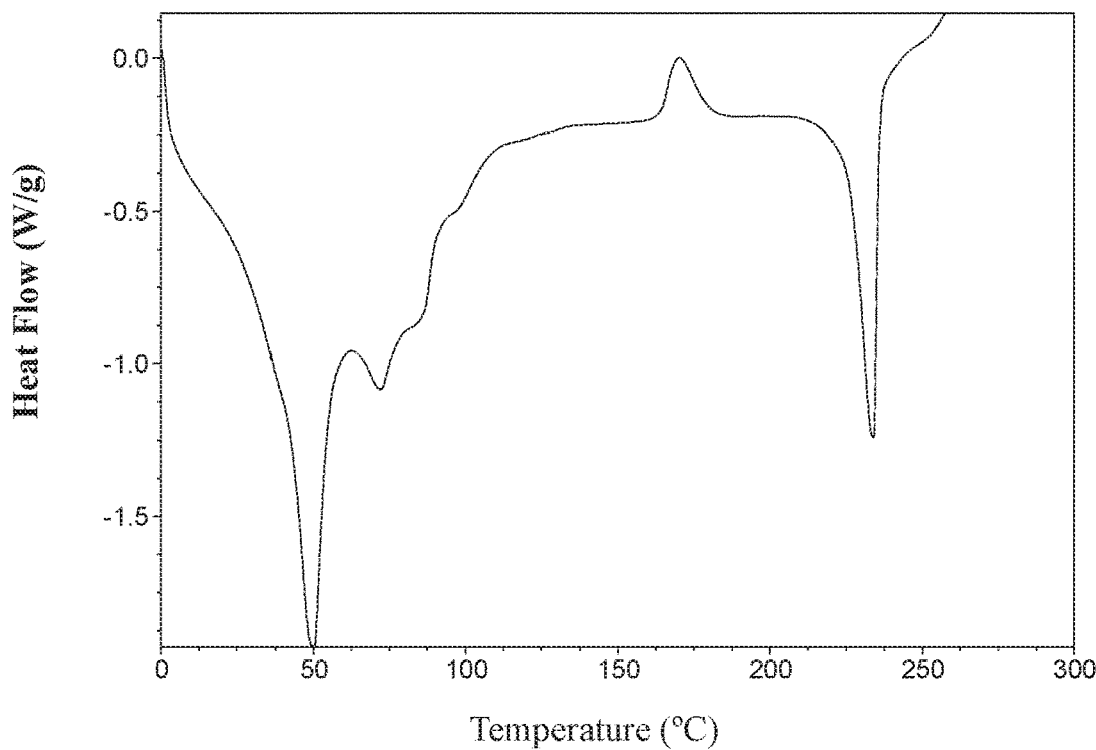
FIG. 4 is a DSC pattern of the sodium salt of the compound represented by formula A according to Example 3 of the present application.

A DSC pattern of the sodium salt was as illustrated in FIG. 4.

Example 4: Preparation of Sodium Salt of the Compound Represented by Formula A 3.5 mg of sodium hydroxide was weighed and added into 1.0 mL of acetone, water (4:1), and ultrasonication was performed to obtain a clear solution. The clear solution was dropped into 29.2 mg of the compound represented by formula A prepared in Preparation Example 1, and the obtained mixture was stirred for 16 h at room temperature. Filtration was performed, and the filter cake obtained was dried for 1 h at 40° C. under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 5: Preparation of Sodium Salt of the Compound Represented by Formula A 5.05 mg of the compound represented by formula A prepared in Preparation Example 1 were weighed and added into 0.2 mL of diethyl ether:ethanol (4:1), and the obtained mixture was stirred to form a suspension. A sodium hydroxide solution (0.65 mg of sodium hydroxide was added into 0.3 mL of diethyl ether:ethanol (4:1 by volume)) was dropped into the suspension of the compound represented by formula A in diethyl ether:ethanol, and the obtained mixture was stirred for 24 h at room temperature. Filtration was performed, and the solvents were removed from the filtrate through volatilization at 60° C. The solid obtained was slurried with 0.2 mL of diethyl ether for 1 h, then centrifugation was performed, and the solid obtained after centrifugation was dried for 19 h at room temperature under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 6: Preparation of Sodium Salt of the Compound Represented by Formula A 8.02 mg of the compound represented by formula A prepared in Preparation Example 1 were weighed. 8.0 mL of n-butanol:methyl tert-butyl ether (1:1) and 2.5 mg of sodium hydroxide were added into the compound, and the obtained mixture was stirred for 1 h at 60° C. Filtration was performed, and the solvents were removed from the filtrate through rotary evaporation at 60° C. The solid obtained was slurried with 0.2 mL of n-butanol:methyl tert-butyl ether (1:1) for 1 h, then centrifugation was performed, and the solid obtained after centrifugation was dried for 48 h at 40° C. under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 7: Preparation of Sodium Salt of the Compound Represented by Formula A 45.01 mg of the compound represented by formula A prepared in Preparation Example 1 were weighed. 0.9 mL of butanone:n-propanol (2:1) and 19.5 mg of sodium hydroxide were added into the compound, and the obtained mixture was stirred for 48 h at 60° C. Filtration was performed, and the solvents were removed from the filtrate through rotary evaporation at room temperature. The solid obtained was slurried with 0.2 mL of butanone:n-propanol (2:1) for 1 h, then centrifugation was performed, and the solid obtained after centrifugation was dried for 40 h at 60° C. under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 8: Preparation of Sodium Salt of the Compound Represented by Formula A 4.69 mg of sodium hydroxide was weighed and added into 1.0 mL of water, and ultrasonication was performed to obtain a clear solution. The clear solution was dropped into 38.77 mg of the compound represented by formula A prepared in Preparation Example 1, then 14.0 mL of water were added, and the obtained mixture was stirred for 16 h at room temperature. Filtration was performed, and the solvent was removed from the filtrate by nitrogen blowing at 50° C. to obtain 0.2 mL of a light yellow transparent clear solution. The solution is cooled to 5° C. to precipitate a solid, then centrifugation was performed, and the solid obtained was dried for 24 h at 40° C. under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 9: Preparation of Sodium Salt of the Compound Represented by Formula A 6.15 mg of the compound represented by formula A prepared in Preparation Example 1 were weighed. 3.0 mL of methanol:isopropyl ether (1:1) and 1.3 mg of sodium hydroxide solid were added into the compound, and the obtained mixture was stirred for 1 h at 40° C. Filtration was performed, and the solvents were removed from the filtrate through rotary evaporation at 50° C. The solid obtained was slurried with 0.1 mL of methanol:isopropyl ether (1:1) for 1 h, then centrifugation was performed, and the solid obtained after centrifugation was dried for 24 h at 25° C. under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 10: Preparation of Sodium Salt of the Compound Represented by Formula A 35.62 mg of the compound represented by formula A prepared in Preparation Example 1 were weighed. 1.2 mL of acetonitrile and 8.7 mg of sodium hydroxide solid were added into the compound, and the obtained mixture was stirred for 3 h at 35° C. Filtration was performed, and the solvent was removed from the filtrate through rotary evaporation at room temperature to obtain 0.2 mL of a colorless transparent clear solution. The solution was cooled to 5° C. to precipitate a solid, then centrifugation was performed, and the solid obtained was dried for 30 h at 40° C. under vacuum to obtain a sodium salt of the compound represented by formula A according to the present application.

IC characterization showed that the sodium salt of the compound represented by formula A was formed through the reaction of the compound represented by formula A and sodium ion in a molar ratio of 1:1.

Example 11: Preparation of Sulfate of the Compound Represented by Formula A 76.02 mg of the compound represented by formula A prepared in Preparation Example 1 was weighed and added into 5.2 mL of methanol, and the obtained mixture was stirred to form a suspension. A sulfuric acid solution (7.3 mg of 98% sulfuric acid was added into 7.6 mL of methanol) was dropped into the suspension of the compound represented by formula A in methanol, and the obtained mixture was stirred for 5 h at room temperature to obtain a suspension. The suspension was stirred for additional 1 h after addition of 5.0 mL of methanol, then filtration was performed, and the solvent was removed from the filtrate by nitrogen blowing at room temperature to obtain 1.0 mL of a suspension. Filtration was performed, and the solid obtained was dried for 20 h at room temperature under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 12: Preparation of Sulfate of the Compound Represented by Formula A 34.41 mg of the compound represented by formula A prepared in Preparation Example 1 were weighed and added into 1.0 mL of ethanol, and the obtained mixture was stirred to form a suspension. 24.82 mg of 98% sulfuric acid was added into the suspension of the compound represented by formula A in ethanol, and the obtained mixture was stirred for 24 h at room temperature. Filtration was performed, and the filter cake obtained was dried for 10 h at 40° C. under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 13: Preparation of Sulfate of the Compound Represented by Formula A 4.63 mg of the compound represented by formula A prepared in Preparation Example 1 were weighed and added into 0.2 mL of n-propanol, and the obtained mixture was stirred to form a suspension. A sulfuric acid solution (8.79 mg of 98% sulfuric acid was added into 0.3 mL of n-propanol) was dropped into the suspension of the compound represented by formula A in n-propanol, and the obtained mixture was stirred for 16 h at room temperature. Filtration was performed, and the solvent was removed from the filtrate by nitrogen blowing at room temperature to obtain an oily substance. Water was added into the oily substance, and ultrasonication was performed to form a suspension. Centrifugation was performed, and the obtained solid was dried for 24 h at room temperature under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Figure 5:
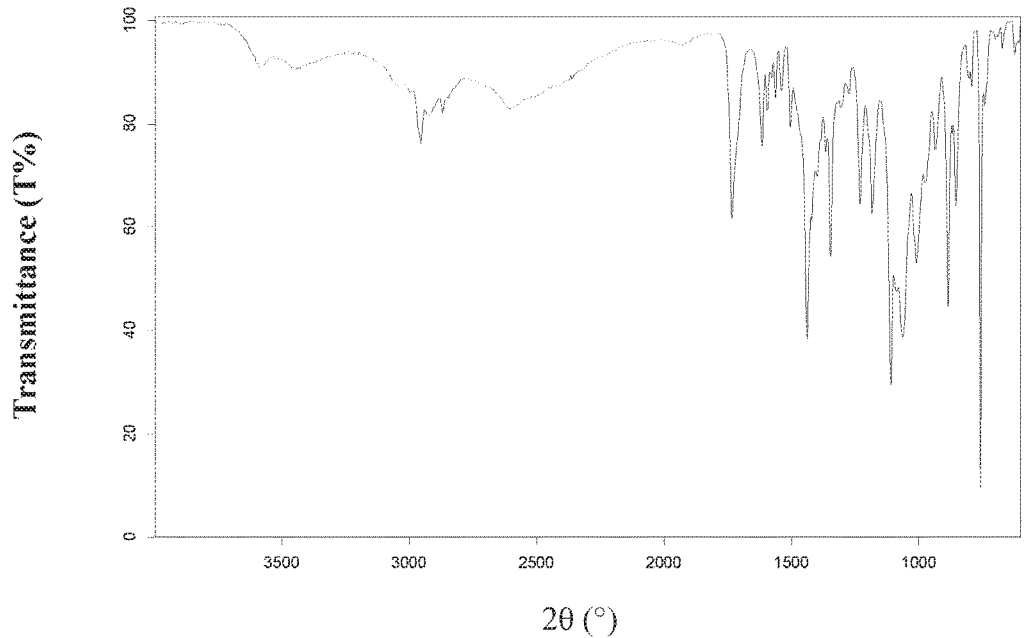
FIG. 5 is an IR pattern of the sulfate of the compound represented by formula A according to Example 13 of the present application.
Figure 6:
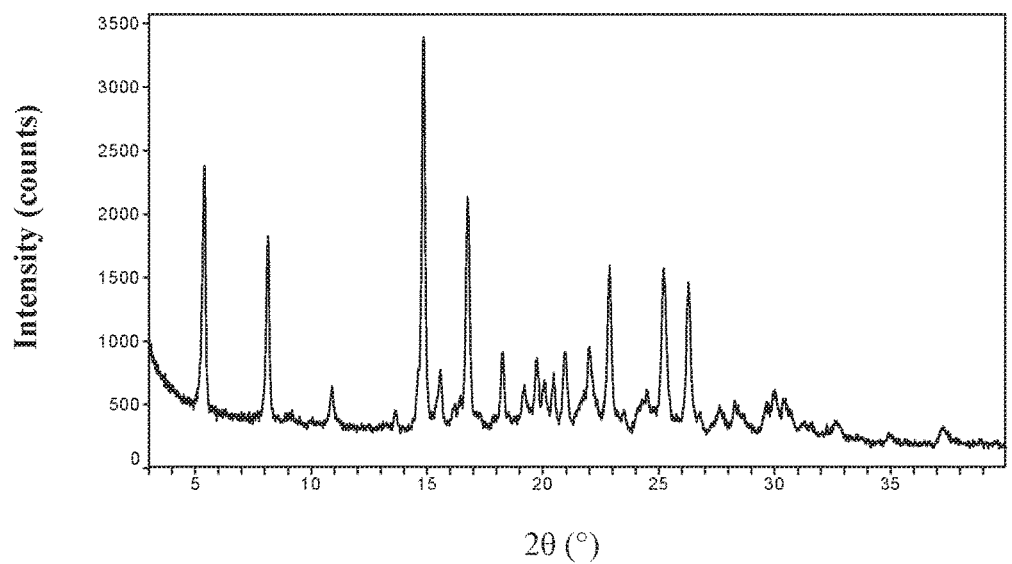
FIG. 6 is an XRPD pattern of the sulfate of the compound represented by formula A according to Example 13 of the present application.
Figure 7:
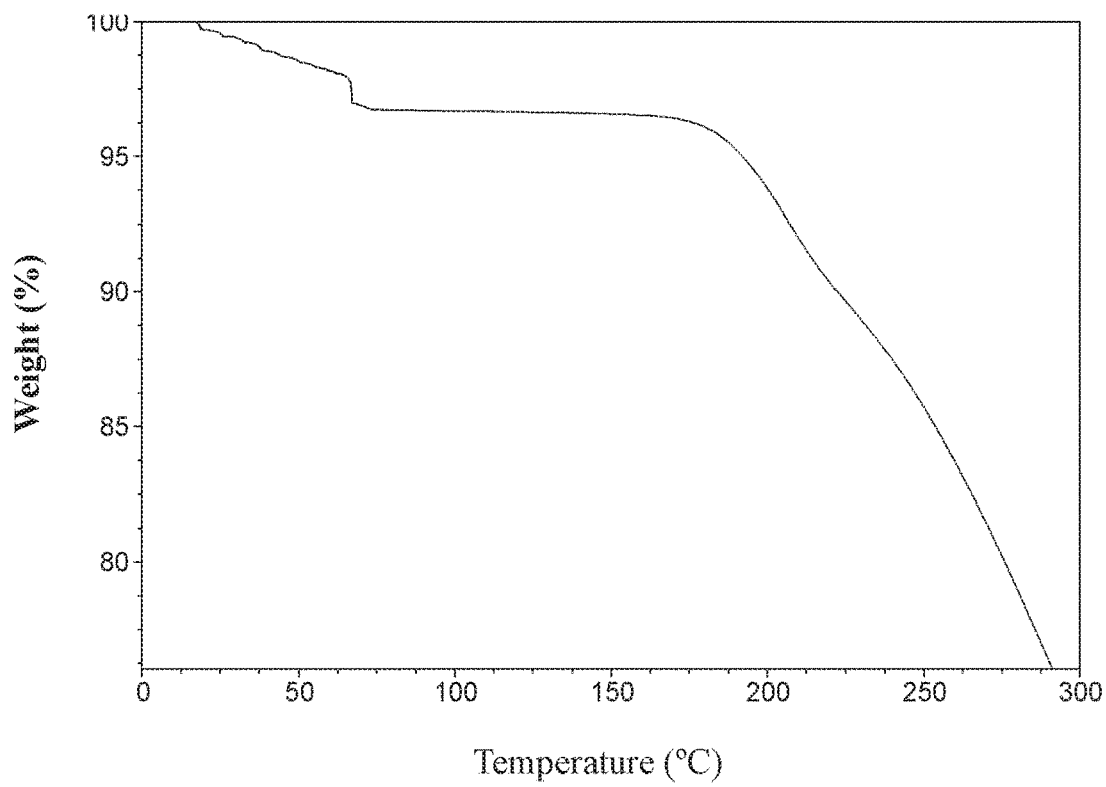
FIG. 7 is a TGA pattern of the sulfate of the compound represented by formula A according to Example 13 of the present application.
Figure 8:
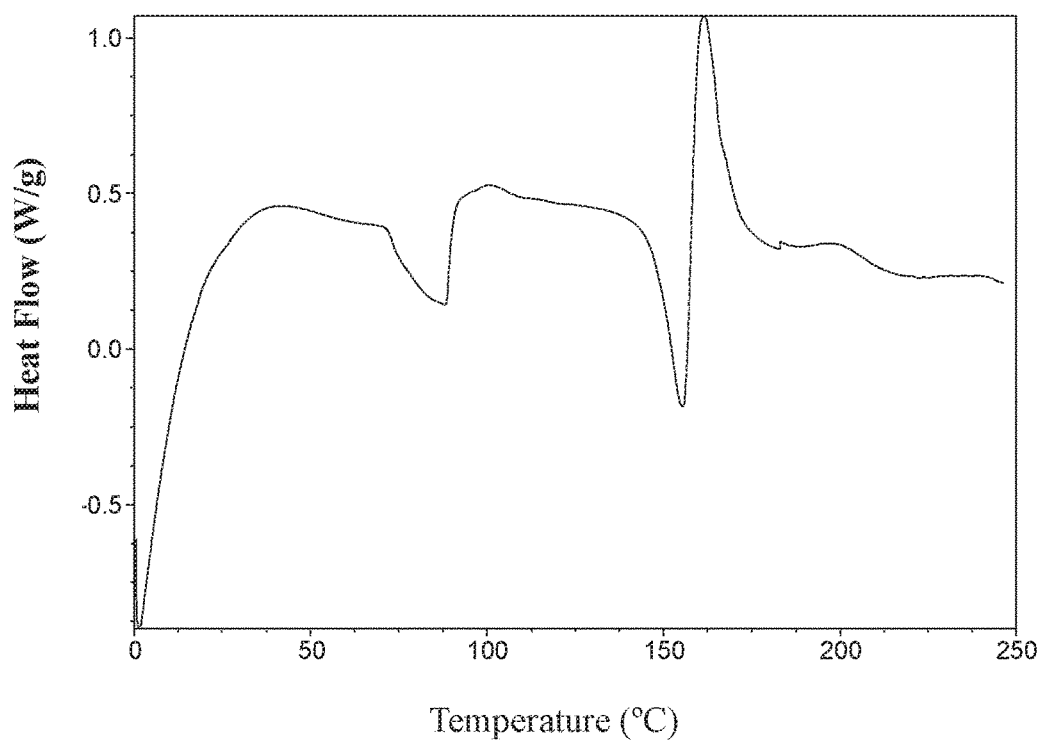
FIG. 8 is a DSC pattern of the sulfate of the compound represented by formula A according to Example 13 of the present application.

An IR pattern of the sulfate was as illustrated in FIG. 5.
An XRD pattern of the sulfate was as illustrated in FIG. 6.
A TGA pattern of the sulfate was as illustrated in FIG. 7.
A DSC pattern of the sulfate was as illustrated in FIG. 8.

Example 14: Preparation of Sulfate of the Compound Represented by Formula A 10.02 mg of the compound represented by formula A prepared in Preparation Example 1 were weighed and added into 1.0 mL of water, and the obtained mixture was stirred to form a suspension. 7.88 mg of 98% sulfuric acid was added into the suspension of the compound represented by formula A in water, and the obtained mixture was stirred for 24 h at 40° C. Filtration was performed, and the filter cake obtained was dried for 1 h at 60° C. under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 15: Preparation of Sulfate of the Compound Represented by Formula A 34.4 mg of the compound represented by formula A prepared in Preparation Example 1 were weighed and added into 1.0 mL of water, and the obtained mixture was stirred to form a suspension. A sulfuric acid solution (25.0 mg of 98% sulfuric acid was added into 0.5 mL of water) was dropped into the suspension of the compound represented by formula A in water, and the obtained mixture was stirred for 24 h at room temperature. Filtration was performed, and the filter cake obtained was dried for 1 h at 40° C. under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 16: Preparation of Sulfate of the Compound Represented by Formula A 10.25 mg of the compound represented by formula A prepared in Preparation Example 1 were weighed and added into 0.2 mL of water, and the obtained mixture was stirred to form a suspension. 8.25 mg of 98% sulfuric acid and 1.0 mL of acetone were sequentially added into the suspension of the compound represented by formula A in water, and the obtained mixture was stirred for 1 h at room temperature to obtain a clear solution. Filtration was performed, then the solvents were removed from the filtrate by nitrogen blowing at room temperature, and the solid obtained was dried for 24 h at room temperature under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 17: Preparation of Sulfate of the Compound Represented by Formula A 10.40 mg of the compound represented by formula A prepared in Preparation Example 1 were weighed. 0.2 mL of water, 7.92 mg of 98% sulfuric acid and 1.0 mL of tetrahydrofuran were sequentially added into the compound represented by formula A, and the obtained mixture was stirred for 3 h at room temperature to obtain a clear solution. Filtration was performed, and the solvents were removed from the filtrate by nitrogen blowing at 60° C. to obtain 0.3 mL of a suspension. Centrifugation was performed, and the solid obtained was dried for 20 h at 40° C. under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 18: Preparation of Sulfate of the Compound Represented by Formula A 4.15 mg of the compound represented by formula A prepared in Preparation Example 1 were weighed and added into 0.2 mL of water:acetonitrile (1:4), and the obtained mixture was stirred to form a suspension. A sulfuric acid solution (3.2 mg of 98% sulfuric acid was added into 0.3 mL of water:acetonitrile (1:4)) was dropped into the suspension of the compound represented by formula A in water:acetonitrile (1:4), and the obtained mixture was stirred for 24 h at room temperature. Filtration was performed, and the solvents were removed from the filtrate by nitrogen blowing at room temperature to obtain 0.1 mL of a suspension. Centrifugation was performed, and the solid obtained was dried for 1 h at 50° C. under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 19: Preparation of Sulfate of the Compound Represented by Formula A 5.0 mg of the compound represented by formula A prepared in Preparation Example 1 were weighed. 5.0 mL of s-butanol:butanone (1:4) and 10.3 mg of 98% sulfuric acid were added into the compound, and the obtained mixture was stirred for 30 h at −10° C. Filtration was performed, and the solvents were removed from the filtrate by nitrogen blowing at 40° C. to obtain 0.1 mL of a suspension. Centrifugation was performed, and the solid obtained was dried for 10 h at 60° C. under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 20: Preparation of Sulfate of the Compound Represented by Formula A 40.0 mg of the compound represented by formula A prepared in Preparation Example 1 were weighed and added into 0.4 mL of 1,4-dioxane:water (1:1), and the obtained mixture was stirred to form a suspension. A sulfuric acid solution (96.7 mg of 98% sulfuric acid was added into 0.4 mL of 1,4-dioxane:water (1:1)) was dropped into the suspension of the compound represented by formula A in 1,4-dioxane:water (1:1), and the obtained mixture was stirred for 72 h at 60° C. Filtration was performed, and the solvents were removed from the filtrate by nitrogen blowing at 60° C. The solid obtained was slurried with 0.2 mL of 1,4-dioxane:water (1:1) for 1 h, then centrifugation was performed, and the solid obtained after centrifugation was dried for 48 h at 40° C. under vacuum to obtain a sulfate of the compound represented by formula A according to the present application.

IC characterization showed that the sulfate of the compound represented by formula A was formed through the reaction of the compound represented by formula A and sulfuric acid in a molar ratio of 2:1.

Example 21: Preparation of Maleate of the Compound Represented by Formula A 51.7 mg of the compound represented by formula A prepared in Preparation Example 1 were weighed and added into 1.0 mL of acetone. A maleic acid solution (17.7 mg of maleic acid was added into 1.0 mL of acetone) was dropped into the system of the compound represented by formula A in acetone under stirring, and the obtained mixture was stirred for 24 h at room temperature. Filtration was performed, and drying was performed for 16 h at 40° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Figure 9:
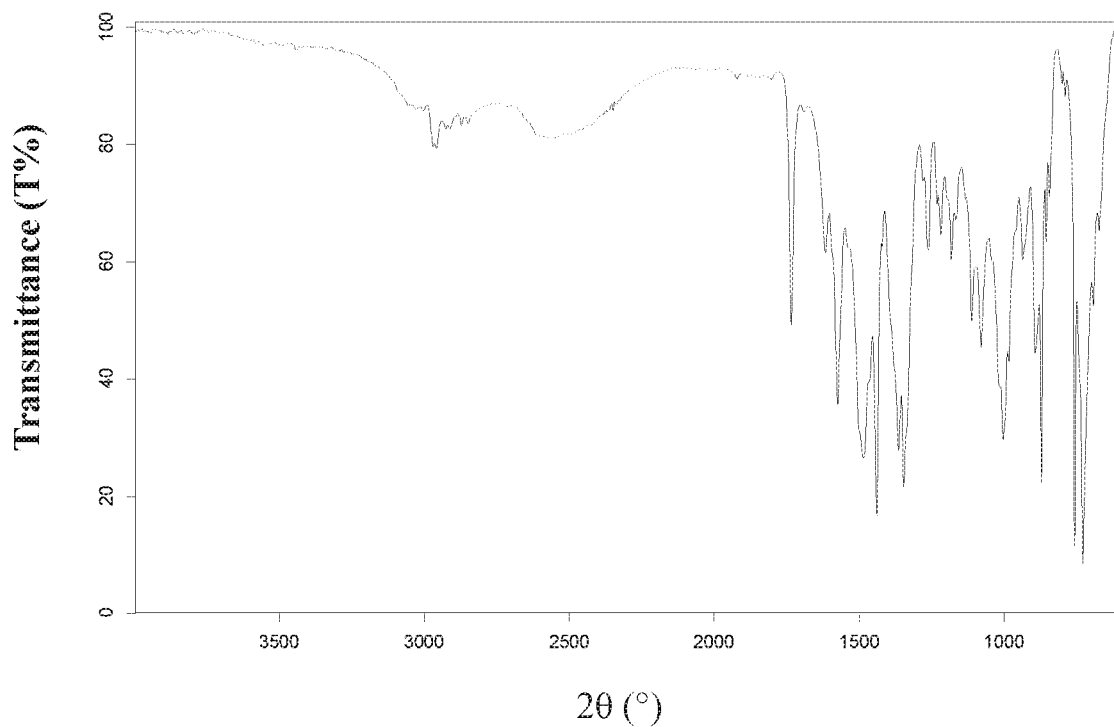
FIG. 9 is an IR pattern of the maleate of the compound represented by formula A according to Example 21 of the present application.
Figure 10:
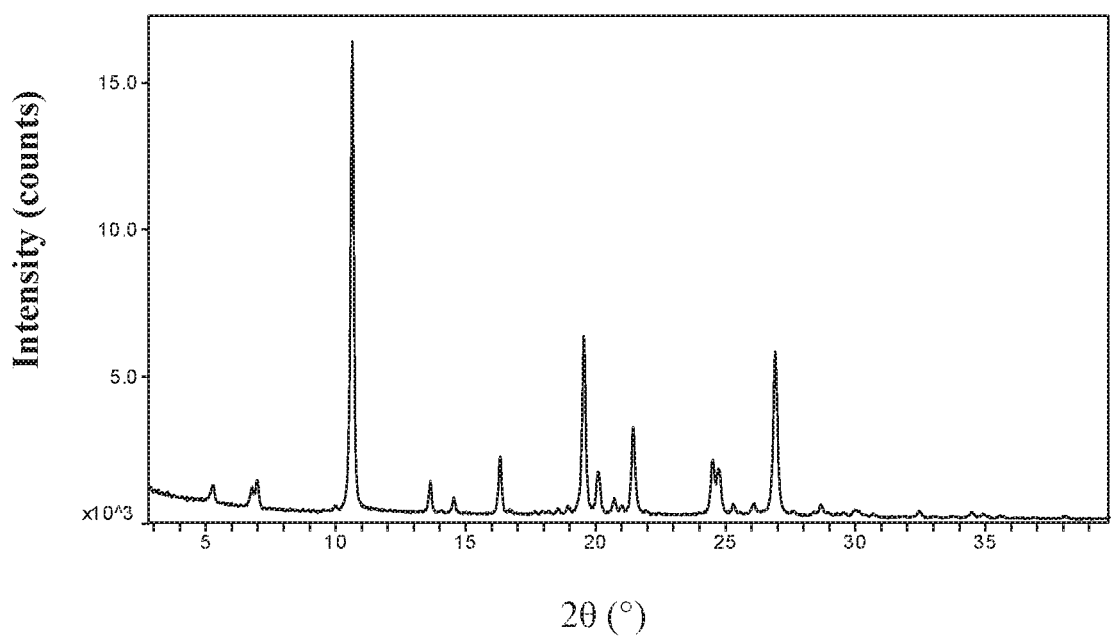
FIG. 10 is an XRPD pattern of the maleate of the compound represented by formula A according to Example 21 of the present application.
Figure 11:
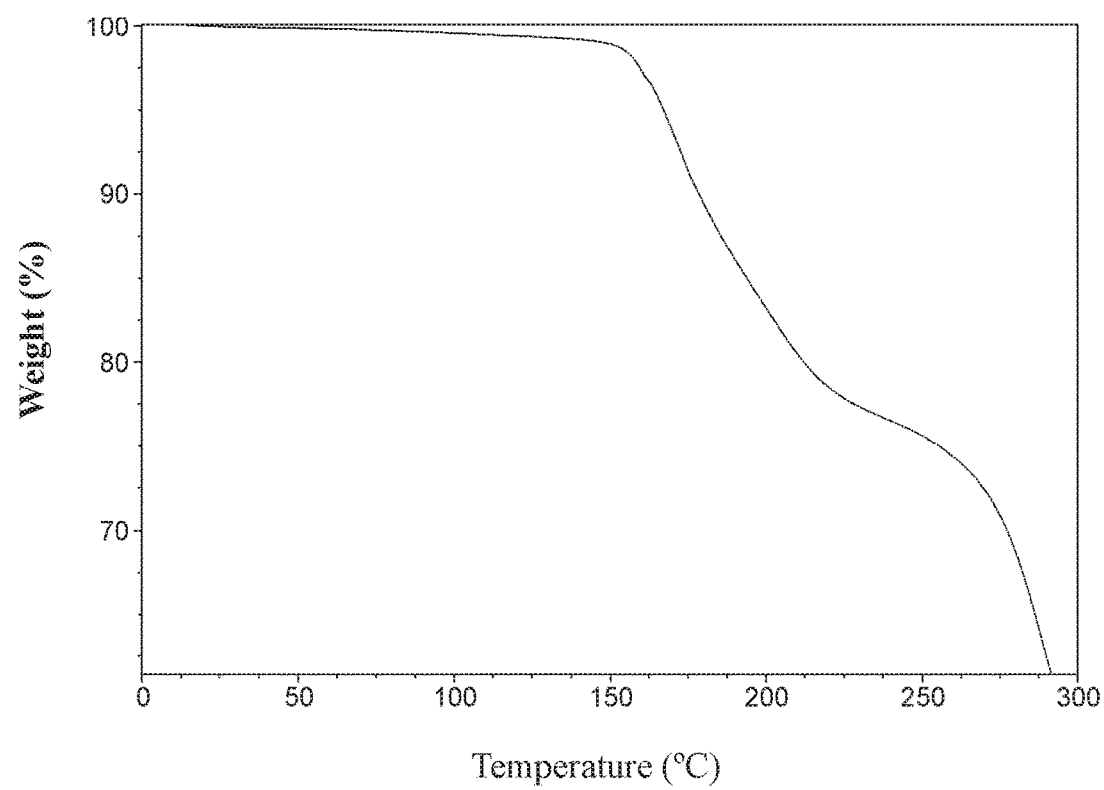
FIG. 11 is a TGA pattern of the maleate of the compound represented by formula A according to Example 21 of the present application.
Figure 12:
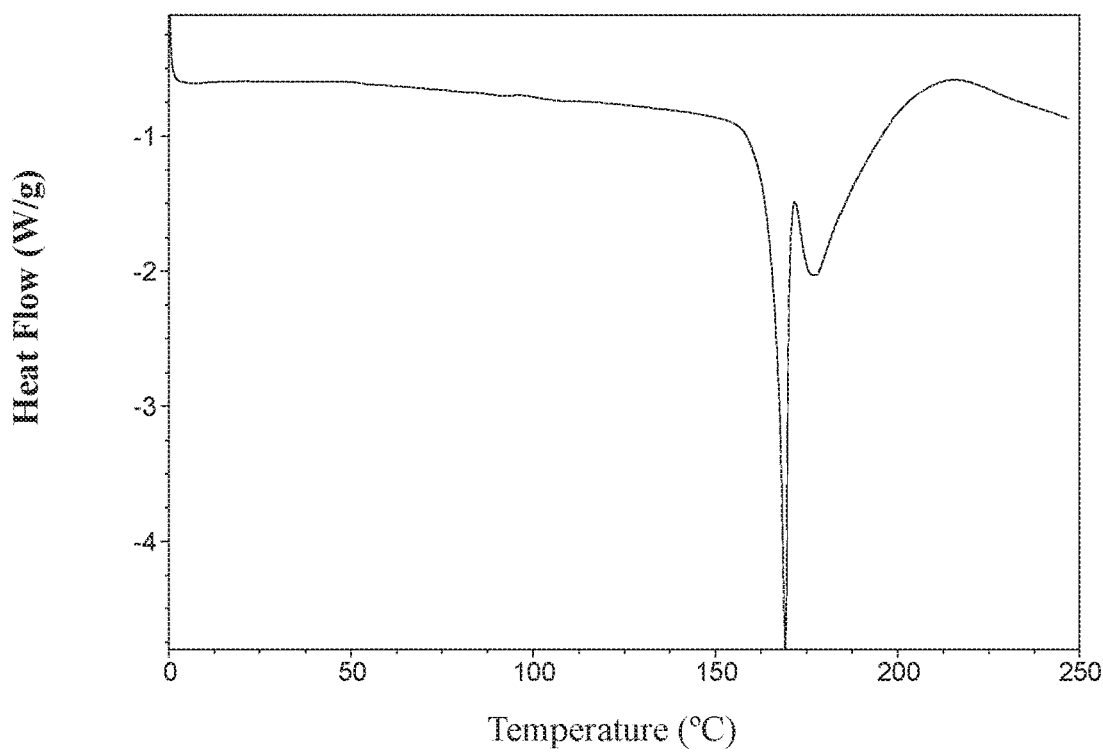
FIG. 12 is a DSC pattern of the maleate of the compound represented by formula A according to Example 21 of the present application.

An IR pattern of the maleate was as illustrated in FIG. 9.
An XRD pattern of the maleate was as illustrated in FIG. 10.
A TGA pattern of the maleate was as illustrated in FIG. 11.
A DSC pattern of the maleate was as illustrated in FIG. 12.

Example 22: Preparation of Maleate of the Compound Represented by Formula A 10.37 mg of the compound represented by formula A prepared in Preparation Example 1 were weighed. A maleic acid solution (3.91 mg of maleic acid was added into 1.0 mL of ethanol) was dropped into the compound, and the obtained mixture was stirred for 10 h at room temperature. Filtration was performed, and the filter cake obtained was dried for 20 h at 25° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Example 23: Preparation of Maleate of the Compound Represented by Formula A 7.63 mg of the compound represented by formula A prepared in Preparation Example 1 were weighed. A maleic acid solution (4.47 mg of maleic acid was added into 1.0 mL of water) was dropped into the compound, and the obtained mixture was stirred for 24 h at 40° C. Filtration was performed, and the filter cake obtained was dried for 1 h at 40° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Example 24: Preparation of Maleate of the Compound Represented by Formula A 10.70 mg of the compound represented by formula A prepared in Preparation Example 1 were weighed. 3.52 mg of maleic acid and 1.0 mL of diethyl ether were added into the compound, and the obtained mixture was stirred for 24 h at room temperature. Filtration was performed, and the filter cake obtained was dried for 24 h at 10° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Example 25: Preparation of Maleate of the Compound Represented by Formula A 13.33 mg of the compound represented by formula A prepared in Preparation Example 1 were weighed and added into 1.5 mL of ethyl acetate. A maleic acid solution (5.14 mg of maleic acid was added into 1.0 mL of ethyl acetate) was dropped into the system of the compound represented by formula A in ethyl acetate under stirring, and the obtained mixture was stirred for 18 h at room temperature. Filtration was performed, and the filter cake obtained was dried for 1 h at 40° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Example 26: Preparation of Maleate of the Compound Represented by Formula A 6.04 mg of the compound represented by formula A prepared in Preparation Example 1 were weighed and added into 1.0 mL of 1,4-dioxane. A maleic acid solution (4.4 mg of maleic acid was added into 0.4 mL of 1,4-dioxane) was dropped into the system of the compound represented by formula A in 1,4-dioxane under stirring, and the obtained mixture was stirred for 20 h at room temperature. Filtration was performed, and the filter cake obtained was dried for 24 h at 50° C. under vacuum to obtain 34.3 mg of a maleate of the compound represented by formula A according to the present application.

IC characterization showed that the maleate of the compound represented by formula A was formed through the reaction of the compound represented by formula A and maleic acid in a molar ratio of 1:1.

Example 27: Preparation of Maleate of the Compound Represented by Formula A 5.0 mg of the compound represented by formula A prepared in Preparation Example 1 were weighed. 4.7 mg of maleic acid and 5.0 mL of butanone:methyl formate (2:1) were added into the compound, and the obtained mixture was stirred for 30 h at 60° C. Filtration was performed, and drying was performed for 37 h at 56° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Example 28: Preparation of Maleate of the Compound Represented by Formula A 40.5 mg of the compound represented by formula A prepared in Preparation Example 1 were weighed and added into 0.6 mL of methanol:methyl tert-butyl ether (1:1). A maleic acid solution (11.5 mg of maleic acid was added into 0.4 mL of methanol:methyl tert-butyl ether (1:1)) was dropped into the system of the compound represented by formula A in methanol:methyl tert-butyl ether (1:1) under stirring, and the obtained mixture was stirred for 48 h at 45° C. Filtration was performed, and drying was performed for 48 h at 40° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Example 29: Preparation of Maleate of the Compound Represented by Formula A 50.0 mg of the compound represented by formula A prepared in Preparation Example 1 were weighed and added into 0.5 mL of n-butanol:isopropyl acetate (3:1). A maleic acid solution (70.9 mg of maleic acid was added into 0.5 mL of n-butanol:isopropyl acetate (3:1)) was dropped into the system of the compound represented by formula A in n-butanol:isopropyl acetate (3:1) under stirring, and the obtained mixture was stirred for 72 h at −10° C. Filtration was performed, and drying was performed for 30 h at 60° C. under vacuum to obtain a maleate of the compound represented by formula A according to the present application.

IC characterization showed that the maleate of the compound represented by formula A was formed through the reaction of the compound represented by formula A and maleic acid in a molar ratio of 1:1.

Comparative Example 1: Solubility of Sodium Salt of the Compound Represented by Formula A The sodium salt of the compound represented by formula A according to the present application was taken to perform a solubility experiment in water. Specific operation was as follows: 5 mg of the sodium salt of the compound represented by formula A according to the present application was taken and put into a 20 ml glass bottle, and deionized water was gradually added at 25° C. into the bottle, and ultrasonication was performed to obtain a clear solution. The solubility of the sample in water was calculated.

TABLE 2

Solubility of sodium salt of the compound represented by formula A according to the present application in water

| Sample name | Solubility (mg/mL) |
|---|---|
| Sodium salt of the compound represented by formula A | 10 |

It can be seen from Table 2 that the sodium salt of the compound represented by formula A according to the present application has a high solubility, so it has a better bioavailability.

Comparative Example 2: Comparison of Thermal Stability of Salt Forms of the Compound Represented by Formula A The sodium salt of the compound represented by formula A according to the present application and conventional salts (citrate of the compound represented by formula A, phosphate of the compound represented by formula A and hydrochloride of the compound represented by formula A) were taken to perform DSC and TGA assays, and melting point and decomposition temperature data of each salt form were obtained.

TABLE 3

Melting point data of sodium salt and other conventional salts of the compound represented by formula A according to the present application

| Salt form | Melting point (° C.) | Decomposition temperature (° C.) |
|---|---|---|
| Sodium salt of the compound represented by formula A | 234 | 275 |
| Citrate of the compound represented by formula A | 152 | 154 |
| Phosphate of the compound represented by formula A | 160 | 190 |
| Hydrochloride of the compound represented by formula A | 163 | 145 |

It can be seen from Table 3 that, compared with the conventional salts (citrate of the compound represented by formula A, phosphate of the compound represented by formula A and hydrochloride of the compound represented by formula A), the sodium salt of the compound represented by formula A according to the present application has very high melting point and decomposition temperature, so it has a better thermal stability.

Comparative Example 3: Comparison of Solubility of Salt Forms of the Compound Represented by Formula A The known free state of the compound represented by formula A, conventional salts (calcium salt of the compound represented by formula A, citrate of the compound represented by formula A, phosphate of the compound represented by formula A, and hydrochloride of the compound represented by formula A), and the sulfate of the compound represented by formula A and the maleate of the compound represented by formula A according to the present application were taken to perform a solubility experiment in water. Specific operation was as follows: 5 mg of the known free state of the compound represented by formula A, conventional salts (calcium salt of the compound represented by formula A, citrate of the compound represented by formula A, phosphate of the compound represented by formula A, and hydrochloride of the compound represented by formula A), and the sulfate of the compound represented by formula A and the maleate of the compound represented by formula A according to the present application prepared were taken and put into 20 ml glass bottles respectively, and 15 ml of deionized water was added into each of the bottles and stirred for 2 h at 25° C. Then samples were taken and filtered, and the concentrations were detected by HPLC. The solubility of the active ingredient in each of the samples in water was calculated.

TABLE 4

Solubility of free state and salt forms of the compound represented by formula A in water

| Sample name | Solubility (μg/mL) |
| --- | --- |
| Free state of the compound represented by formula A | 1.1 |
| Sulfate of the compound represented by formula A | 19.2 |
| Maleate of the compound represented by formula A | 16.1 |
| Calcium salt of the compound represented by formula A | 2.5 |
| Citrate of the compound represented by formula A | 5.3 |
| Phosphate of the compound represented by formula A | 6.7 |
| Hydrochloride of the compound represented by formula A | 3.8 |

It can be seen from Table 4 that, the solubility of the sulfate of the compound represented by formula A and the maleate of the compound represented by formula A according to the present application in water at 25° C. is about 10-20 times higher than that of the known free state of the compound represented by formula A; and is about 3-8 times higher than those of other conventional salts (calcium salt of the compound represented by formula A, citrate salt of the compound represented by formula A, phosphate of the compound represented by formula A, and hydrochloride of the compound represented by formula A), so the sulfate and the maleate have a better solubility, and a better bioavailability.

Comparative Example 4: Comparison of Hygroscopicity of Salt Forms of the Compound Represented by Formula A The sulfate of the compound represented by formula A and the maleate of the compound represented by formula A according to the present application, and conventional salts (potassium salt of the compound represented by formula A, calcium salt of the compound represented by formula A, citrate of the compound represented by formula A, phosphate of the compound represented by formula A, and hydrochloride of the compound represented by formula A) were taken to perform DVS assay, and hygroscopicity data of each salt form were obtained.

TABLE 5

Hygroscopicity data of sulfate of the compound represented by formula A and maleate of the compound represented by formula A according to the present application, and other conventional salts

| Salt form | Moisture uptake (%) | Appearance |
| --- | --- | --- |
| Sulfate of the compound represented by formula A | 0.7 | Powder |
| Maleate of the compound represented by formula A | 0.4 | Powder |
| Potassium salt of the compound represented by formula A | 17.5 | Deliquesced into a solution |
| Calcium salt of the compound represented by formula A | 1.2 | Powder |
| Citrate of the compound represented by formula A | 0.7 | Powder |
| Phosphate of the compound represented by formula A | 1.2 | Powder |
| Hydrochloride of the compound represented by formula A | 1.2 | Powder |

It can be seen from Table 5 that, compared with conventional salts (potassium salt of the compound represented by formula A, calcium salt of the compound represented by formula A, citrate of the compound represented by formula A, phosphate of the compound represented by formula A, and hydrochloride of the compound represented by formula A), the sulfate of the compound represented by formula A and the maleate of the compound represented by formula A according to the present application have a lower hygroscopic weight gain, thus have better storage stability, and can be better at avoiding quality, safety and stability problems during drug manufacture and/or storage, etc.

Comparative Example 5: Comparison of Stability of Crystal Forms of Salts of the Compound Represented by Formula A The crystal form of the sulfate of the compound represented by formula A and the crystal form of the maleate of the compound represented by formula A according to the present application were taken to perform a stability experiment. Specific operation was as follows: 60 mg of the samples of the crystal form of the sulfate of the compound represented by formula A and the crystal form of the maleate of the compound represented by formula A according to the present application were taken and placed for 30 days respectively under conventional condition (sealed and placed in a dark place at 25° C.), high-temperature condition (sealed and placed in a dark place at 60° C.) and accelerated condition (opened and placed in a dark place at 40° C.-75% relative humidity) to study crystal form stability.

TABLE 6

Results of stability test of crystal form of sulfate of the compound represented by formula A and crystal form of maleate of the compound represented by formula A according to the present application

| Stability condition | Sulfate of the compound represented by formula A | | Maleate of the compound represented by formula A | |
| --- | --- | --- | --- | --- |
| | Crystal form | Melting point | Crystal form | Melting point |
| Conventional | No obvious change | No obvious change | No obvious change | No obvious change |
| High-temperature | No obvious change | No obvious change | No obvious change | No obvious change |
| Accelerated | No obvious change | No obvious change | No obvious change | No obvious change |

It can be seen from Table 6 that, the crystal form of the sulfate of the compound represented by formula A and the crystal form of the maleate of the compound represented by formula A according to the present application have good stability, which is beneficial to adapt to various environmental conditions during manufacture, storage and transportation.

Comparative Example 6: Comparison of Stability of Crystal Forms of Salts of the Compound Represented by Formula A The crystal form of the sodium salt of the compound represented by formula A, the crystal form of the sulfate of the compound represented by formula A and the crystal form of the maleate of the compound represented by formula A were respectively taken to form suspensions in solvents as shown in Table 7, and the suspensions were stirred for 3 days at room temperature. Crystal form stability was studied, and results obtained were compared with the results in Comparative Example 1 in patent document CN105315266A.

TABLE 7

Results of crystal form stability test of salt forms of the compound represented by formula A according to the present application and free state of the compound represented by formula A in solvents

| Solvent | Free state of the compound represented by formula A | | | Crystal form of sodium salt of the compound represented by formula A | Crystal form of sulfate of the compound represented by formula A | Crystal form of maleate of the compound represented by formula A |
|---|---|---|---|---|---|---|
| | Crystal form I, crystal form IV, crystal form XII, crystal form II crystal form III, crystal form V, crystal form VI, crystal form VII, crystal form VIII, crystal form IX, crystal form X, crystal form XI and amorphous form | Crystal form XII and crystal form IV | Crystal form XII and crystal form I | | | |
| Isopropanol | Crystal form IV | — | — | No change | No change | No change |
| Water | Crystal form I | Crystal form XII | — | No change | No change | No change |
| Water:ethanol = 1:1 | Crystal form I | — | — | No change | No change | No change |
| Water:ethanol = 1:5 | Crystal form I | — | — | No change | No change | No change |
| Water:ethanol = 1:10 | Crystal form I | — | — | No change | No change | No change |
| Water:ethanol = 1:100 | Crystal form I | — | — | No change | No change | No change |
| Ethanol | Crystal form IV | — | Crystal form IV | No change | No change | No change |
| Water:acetone = 1:1 | Crystal form I | — | — | No change | No change | No change |
| Water:acetone = 1:5 | Crystal form I | — | — | No change | No change | No change |
| Water:acetone = 1:10 | Crystal form I | — | — | No change | No change | No change |
| Water:acetone = 1:100 | Crystal form I | — | — | No change | No change | No change |
| Acetone | Crystal form IV | Crystal form IV | — | No change | No change | No change |

It can be seen from Table 7 that, the free state of the compound represented by formula A is present in various final crystal forms in different solvents, which indicates that the free state of the compound represented by formula A is prone to problems that mixed crystals are formed and crystal form is difficult to control during drug preparation. In contrast, the crystal form of each salt form of the compound represented by formula A according to the present application is relatively single, the selection of solvents to be used in production is more flexible, and the crystal form is more stable.

All patent documents and non-patent publications cited in the description are incorporated herein by reference in their entireties.

What are described above are only particular embodiments of the present application, and the scope of protection of the present application is not limited thereto. Any change or replacement that can be conceived by those skilled in the art within the technical scope disclosed by the present application without any inventive labor shall be covered within the scope of protection of the present application.

The invention claimed is:

1. A maleate of the compound 1-{2-fluoro-4-[5-(4-isobutylphenyl)-1,2,4-oxadiazole-3-yl]benzyl}-3-azetidinecarboxylic acid, having a structure represented by the following formula:

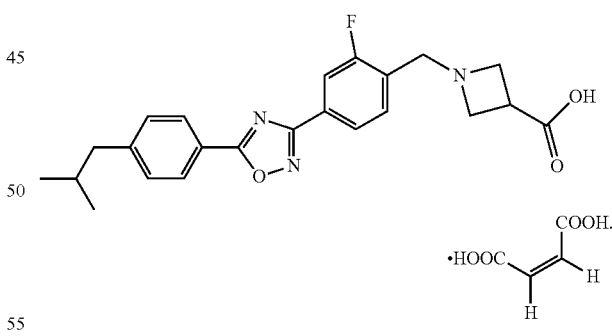

2. The maleate according to claim 1, wherein the maleate is substantially a crystal form, wherein with Cu-Kα radiation, the crystal form has an X-ray powder diffraction pattern characterized by angle 2θ having characteristic peaks at the following positions: 10.6±0.2°, 16.3±0.2°, 19.5±0.2°, 21.5±0.2°, and 26.9±0.2°.

3. The maleate according to claim 2, wherein the crystal form has an X-ray powder diffraction pattern characterized by angle 2θ having characteristic peaks at the following positions: 7.0±0.2°, 10.6±0.2°, 13.6±0.2°, 16.3±0.2°, 19.5±0.2°, 20.1±0.2°, 21.5±0.2°, 24.5±0.2°, and 26.9±0.2°.

4. The maleate according to claim 2, wherein the crystal form has a Fourier transform infrared spectrum having characteristic peaks at wavenumbers 1734 cm$^{-1}$, 1574 cm$^{-1}$, 1485 cm$^{-1}$, 1439 cm$^{-1}$, 1364 cm$^{-1}$, 1346 cm$^{-1}$, 1080 cm$^{-1}$, 1003 cm$^{-1}$, 893 cm$^{-1}$, 871 cm$^{-1}$, 757 cm$^{-1}$, and 729 cm$^{-1}$.

5. A method for preparing the maleate according to claim 1, comprising the following steps:
forming a suspension or solution of the compound 1-{2-fluoro-4-[5-(4-isobutylphenyl)-1,2,4-oxadiazole-3-yl]benzyl}-3-azetidinecarboxylic acid in a solvent selected from the group consisting of a $C_1$-$C_4$ alcohol, a $C_3$-$C_4$ ketone, $C_4$-$C_6$ ether, a $C_2$-$C_5$ ester, and water, and mixtures thereof and a suspension or solution of maleic acid in a solvent selected from the group consisting of a $C_1$-$C_4$ alcohol, a $C_3$-$C_4$ ketone, $C_4$-$C_6$ ether, a $C_2$-$C_5$ ester, and water, and mixtures thereof;
mixing the suspension or solution of the compound 1-{2-fluoro-4-[5-(4-isobutylphenyl)-1,2,4-oxadiazole-3-yl]benzyl}-3-azetidinecarboxylic acid and the suspension or solution of maleic acid in a molar ratio of 1:1 to 1:5 of the compound 1-{2-fluoro-4-[5-(4-isobutylphenyl)-1,2,4-oxadiazole-3-yl]benzyl}-3-azetidinecarboxylic acid to maleic acid for reaction;
removing the solvent after the reaction is complete; and performing drying.

6. The maleate according to claim 2, wherein the crystal form has an X-ray powder diffraction pattern characterized by angle 2θ having characteristic peaks at the following positions with relative intensities as follows:

| 2θ | Relative intensity % |
| --- | --- |
| 5.3 ± 0.2° | 3.4 |
| 7.0 ± 0.2° | 5.8 |
| 10.6 ± 0.2° | 100 |
| 13.6 ± 0.2° | 6.6 |
| 14.5 ± 0.2° | 3.2 |
| 16.3 ± 0.2° | 12.2 |
| 19.5 ± 0.2° | 37.7 |
| 20.1 ± 0.2° | 8.6 |
| 20.7 ± 0.2° | 2.8 |
| 21.5 ± 0.2° | 18.3 |
| 24.5 ± 0.2° | 11.4 |
| 24.7 ± 0.2° | 9.6 |
| 25.3 ± 0.2° | 1.8 |
| 26.1 ± 0.2° | 1.9 |
| 26.9 ± 0.2° | 34.5 |
| 28.7 ± 0.2° | 2.2. |

7. The maleate according to claim 2, wherein the crystal form has an X-ray powder diffraction pattern substantially as illustrated in FIG. 10.

8. The maleate according to claim 1, wherein the maleate is an anhydrate, a hydrate, or a non-solvate.

9. The method according to claim 5, wherein the solvent is selected from the group consisting of ethanol, acetone, ether, water, ethyl acetate, and 1,4-dioxane, and mixtures thereof.

10. The method according to claim 5, wherein the molar ratio of the compound 1-{2-fluoro-4-[5-(4-isobutylphenyl)-1,2,4-oxadiazole-3-yl]benzyl}-3-azetidinecarboxylic acid to maleic acid is 1:1.0 to 1:2.6.

11. The method according to claim 5, wherein the reaction is performed at 10° C. to 60° C.

12. The method according to claim 5, wherein the reaction is performed under stirring.

13. The method according to claim 5, wherein the drying is performed at a temperature of 10° C. to 60° C.

14. The method according to claim 5, wherein the ratio of mass of the compound 1-{2-fluoro-4-[5-(4-isobutylphenyl)-1,2,4-oxadiazole-3-yl]benzyl}-3-azetidinecarboxylic acid to volume of the solvent in the method is 1 mg:1 mL to 50 mg:1 mL.

* * * * *